(12) United States Patent
Hoehse et al.

(10) Patent No.: US 11,680,240 B2
(45) Date of Patent: Jun. 20, 2023

(54) CONTAINER HAVING WALL PROTRUSION AND SENSOR REGION

(71) Applicant: Sartorius Stedim Biotech GmbH, Göttingen (DE)

(72) Inventors: Marek Hoehse, Göttingen (DE); Thomas Regen, Göttingen (DE)

(73) Assignee: Sartorius Stedim Biotech GmbH

( * ) Notice: Subject to any disclaimer, the term of this patent is extended or adjusted under 35 U.S.C. 154(b) by 462 days.

(21) Appl. No.: 16/764,822

(22) PCT Filed: Aug. 31, 2018

(86) PCT No.: PCT/EP2018/073412
§ 371 (c)(1),
(2) Date: May 15, 2020

(87) PCT Pub. No.: WO2019/096457
PCT Pub. Date: May 23, 2019

(65) Prior Publication Data
US 2020/0362292 A1 Nov. 19, 2020

(30) Foreign Application Priority Data
Nov. 16, 2017 (DE) ...................... 10 2017 010 629.0

(51) Int. Cl.
*C12M 1/34* (2006.01)
*C12M 1/00* (2006.01)
(Continued)

(52) U.S. Cl.
CPC ............ *C12M 41/30* (2013.01); *C12M 23/14* (2013.01); *C12M 23/22* (2013.01); *C12M 41/48* (2013.01);
(Continued)

(58) Field of Classification Search
CPC ...... C12M 23/14; C12M 23/28; C12M 23/26; C12M 27/02; C12M 41/00; C12M 23/22;
(Continued)

(56) References Cited

U.S. PATENT DOCUMENTS

| 4,526,480 A | * | 7/1985 | Ward | G01N 9/002 73/32 A |
| 8,542,363 B2 | * | 9/2013 | Wynn | G01N 21/8507 356/440 |

(Continued)

FOREIGN PATENT DOCUMENTS

| CN | 102676386 A | * | 9/2012 | ............ C12M 35/04 |
| CN | 102994367 A | * | 3/2013 | ............ C12M 21/02 |

(Continued)

OTHER PUBLICATIONS

International Search Report, dated Nov. 15, 2018, for International Application No. PCT/EP2018/073412, 5 pages (with English translation).
(Continued)

*Primary Examiner* — Michael P Stafira
(74) *Attorney, Agent, or Firm* — Klarquist Sparkman, LLP

(57) ABSTRACT

A container having at least one wall protrusion for mounting at least one sensor from the outside for sensing at least one variable of a medium contained in a container interior is provided. The wall protrusion can be arranged on a container wall and configured to at least partly extend around the container interior and the medium. The wall protrusion can include at least one sensor region that is configured so that the at least one variable can be sensed through the sensor region by means of the sensor.

20 Claims, 11 Drawing Sheets

Figure 1:
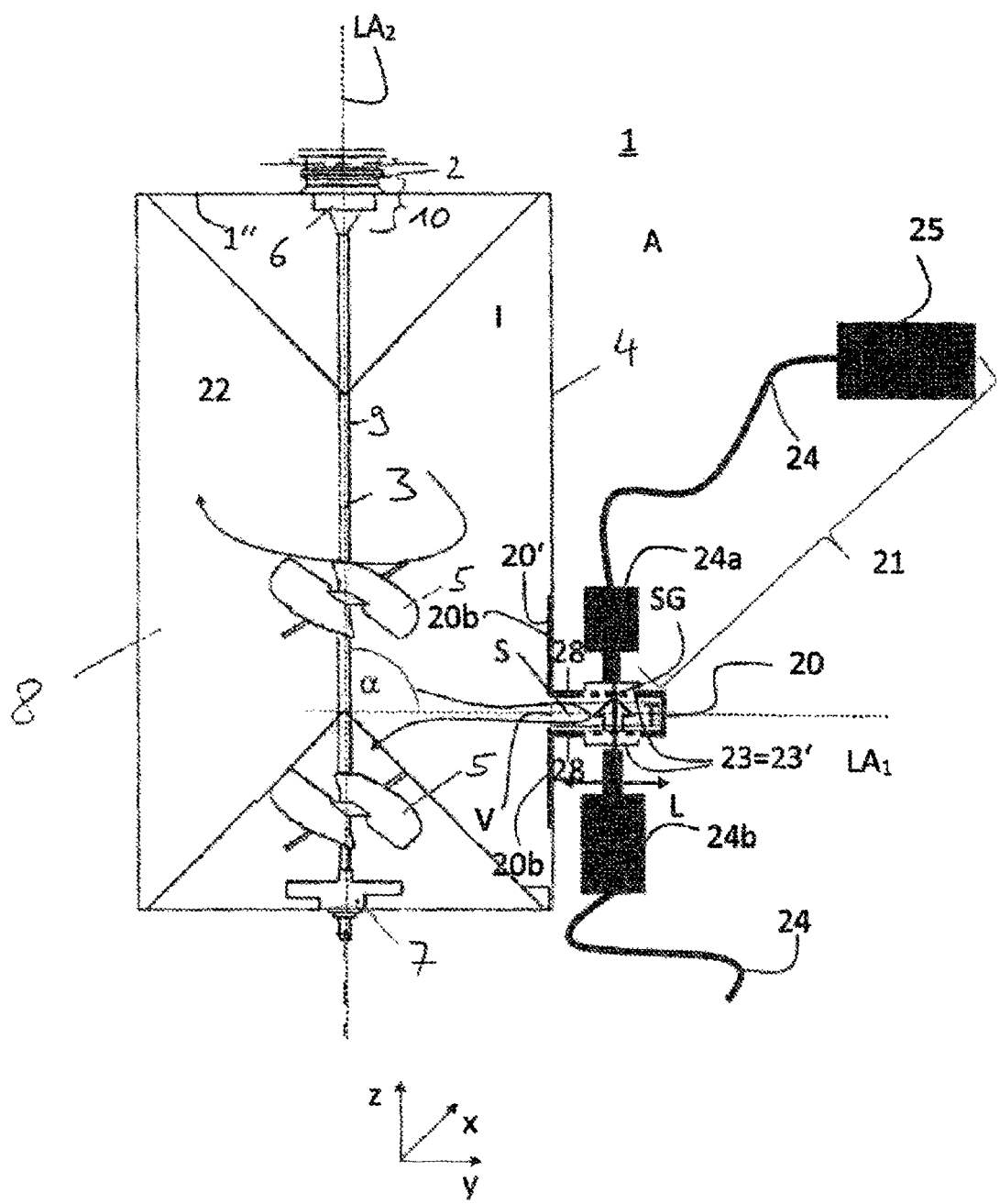

(51) Int. Cl.
| | |
|---|---|
| *C12M 1/36* | (2006.01) |
| *G01N 21/03* | (2006.01) |
| *G01N 21/05* | (2006.01) |
| *G01N 21/31* | (2006.01) |
| *G01N 21/64* | (2006.01) |

(52) U.S. Cl.
CPC ......... *G01N 21/0303* (2013.01); *G01N 21/05* (2013.01); *G01N 21/31* (2013.01); *G01N 21/64* (2013.01); *G01N 2021/0364* (2013.01); *G01N 2201/08* (2013.01)

(58) Field of Classification Search
CPC ...... C12M 21/08; C12M 23/38; C12M 23/48; C12M 37/04; C12M 29/10; C12M 41/46; C12M 41/48; C12M 23/00; C12M 47/10; C12M 27/10; C12M 29/00; C12M 35/04; C12M 41/32; C12M 29/06; C12M 41/14; C12M 23/34; C12M 1/00; C12M 25/14; C12M 21/02; C12M 37/00; C12M 41/40; C12M 27/16; C12M 41/12; C12M 23/42; C12M 25/02; C12M 23/12; C12M 23/46; C12M 41/34; C12M 41/36; C12M 23/02; C12M 23/06; C12M 33/00; C12M 41/26; C12M 23/40; C12M 47/00; C12M 23/16; C12M 29/04; C12M 27/20; C12M 31/10; C12M 43/00; C12M 23/20; C12M 29/14; C12M 23/52; C12M 23/58; C12M 33/10; C12M 33/22; C12M 27/18; C12M 3/00; C12M 33/04; C12M 41/06; C12M 1/34; C12M 29/20; C12M 31/02; C12M 35/02; C12M 37/02; C12M 39/00; C12M 41/24; C12M 31/00; C12M 21/04; C12M 23/44; C12M 43/08; C12M 47/04; C12M 23/24; C12M 23/50; C12M 29/26; C12M 31/08; C12M 33/14; C12M 41/18; C12M 47/02; C12M 27/04; C12M 27/12; C12M 45/02; C12M 45/20; C12M 41/02; C12M 41/44; C12M 29/08; C12M 29/12; C12M 29/18; C12M 29/24; C12M 43/04; C12M 23/04; C12M 23/08; C12M 27/00; C12M 35/06; C12M 41/22; C12M 1/02; C12M 1/12; C12M 25/18; C12M 25/20; C12M 27/14; C12M 29/02; C12M 41/30; C12M 43/02; C12M 1/007; C12M 1/04; C12M 21/00; C12M 21/16; C12M 23/36; C12M 23/54; C12M 25/04; C12M 25/10; C12M 27/06; C12M 27/24; C12M 3/02; C12M 33/07; C12M 41/16; C12M 41/42; C12M 45/06; C12M 47/18; C12M 1/005; C12M 1/06; C12M 1/10; C12M 1/16; C12M 1/18; C12M 1/21; C12M 1/42; C12M 25/16; C12M 27/08; C12M 29/16; C12M 45/22; C12M 21/06; C12M 33/16; C12M 41/08; C12M 1/38; C12M 41/20; G01N 2021/1704; G01N 2021/3129; G01N 2021/513; G01N 2021/9546; G01N 2021/95638; G01N 2033/0078; G01N 2033/0083; G01N 2035/00158; G01N 21/00; G01N 21/35; G01N 21/3563; G01N 21/538; G01N 21/554; G01N 21/88; G01N 21/952; G01N 21/95692; G01N 2201/0616; G01N 2201/06186; G01N 2201/0642; G01N 2203/0005; G01N 2203/0033; G01N 2203/005; G01N 2203/0085; G01N 2203/028; G01N 2203/04; G01N 2291/0232; G01N 2291/02872; G01N 2291/103; G01N 2291/2634; G01N 23/04; G01N 25/18; G01N 27/10; G01N 27/127; G01N 27/28; G01N 27/403; G01N 27/4073; G01N 27/48; G01N 29/14; G01N 29/223; G01N 29/2418; G01N 29/245; G01N 29/2475; G01N 29/46; G01N 3/30; G01N 3/303; G01N 3/32; G01N 3/42; G01N 3/48; G01N 33/18; G01N 33/1833; G01N 33/2028; G01N 33/24; G01N 33/2835; G01N 33/42; G01N 33/487; G01N 33/491; G01N 33/4915; G01N 33/492; G01N 33/5014; G01N 33/502; G01N 33/54373; G01N 33/5438; G01N 35/085; G01N 35/1095; G01N 5/04; G01N 7/18; G01N 9/08; G01N 9/10; G01N 9/26; G01N 9/36

See application file for complete search history.

(56) References Cited

U.S. PATENT DOCUMENTS

| | | | | |
|---|---|---|---|---|
| 8,828,202 | B2* | 9/2014 | Feng | ............... C12M 41/32 204/415 |
| 2004/0017569 | A1 | 1/2004 | Payne | |
| 2012/0242993 | A1* | 9/2012 | Schick | ............... G01N 21/0303 356/442 |
| 2012/0244608 | A1 | 9/2012 | Selker et al. | |
| 2014/0054186 | A1* | 2/2014 | Riechers | ............... C12M 41/00 356/246 |
| 2016/0258870 | A1 | 9/2016 | Tokhtuev et al. | |

FOREIGN PATENT DOCUMENTS

| | | | | |
|---|---|---|---|---|
| DE | 102010044237 A1 | * | 3/2012 | ......... G01N 21/0303 |
| DE | 102010044237 A1 | | 3/2012 | |
| DE | 202012004503 U1 | | 5/2012 | |
| DE | 12011101107 A1 | | 11/2012 | |
| DE | 102015122745 B3 | | 1/2017 | |
| EP | 3045521 A1 | * | 7/2016 | ............ C12M 23/14 |
| JP | H11296657 A | * | 10/1999 | |
| WO | WO-2013042435 A1 | * | 3/2013 | ................ B01L 3/52 |
| WO | WO-2017020019 A1 | * | 2/2017 | ......... A61B 5/14539 |

OTHER PUBLICATIONS

Written Opinion, dated Nov. 15, 2018, for International Application No. PCT/EP2018/073412, 7 pages (with English translation).

* cited by examiner

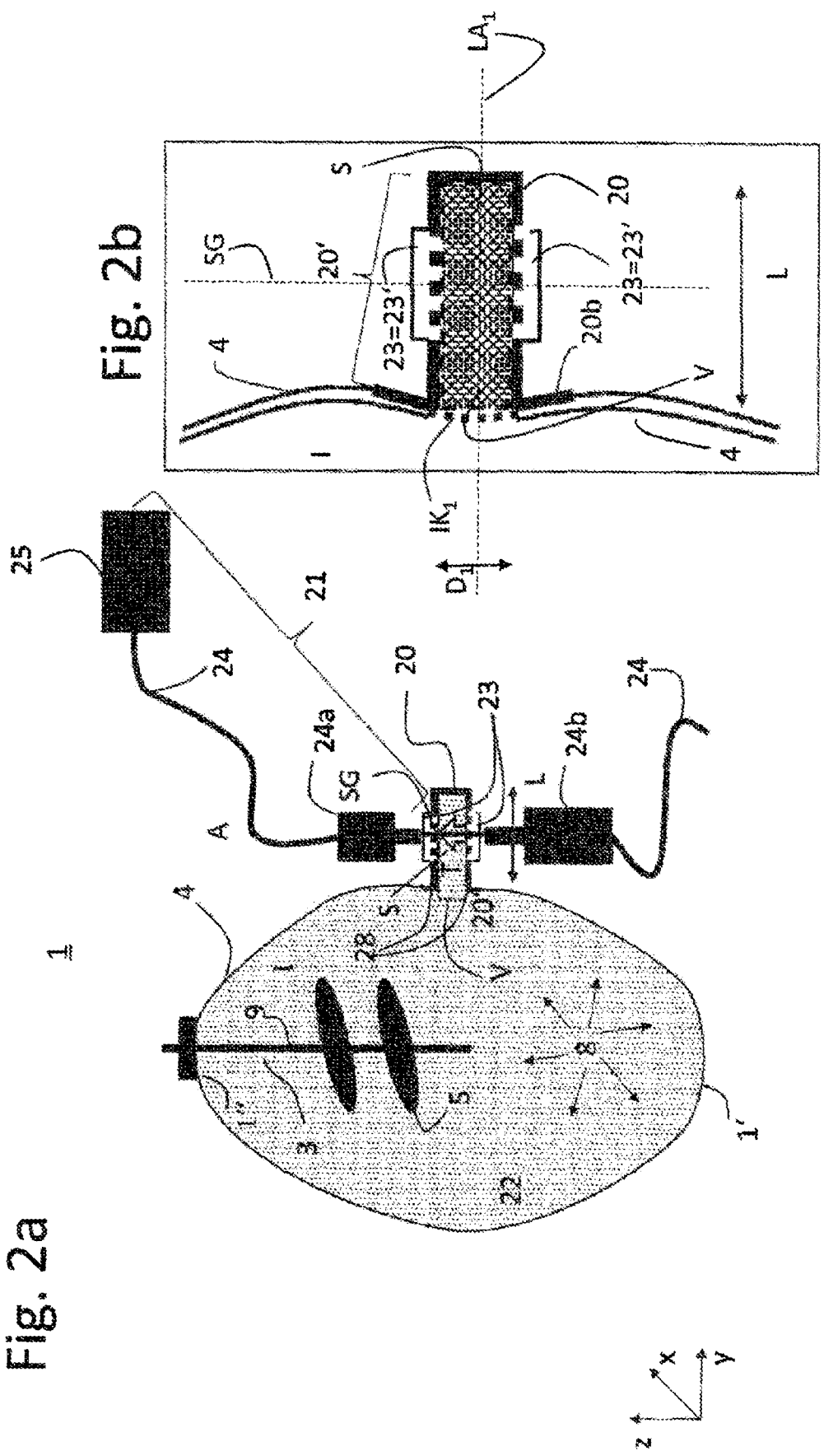

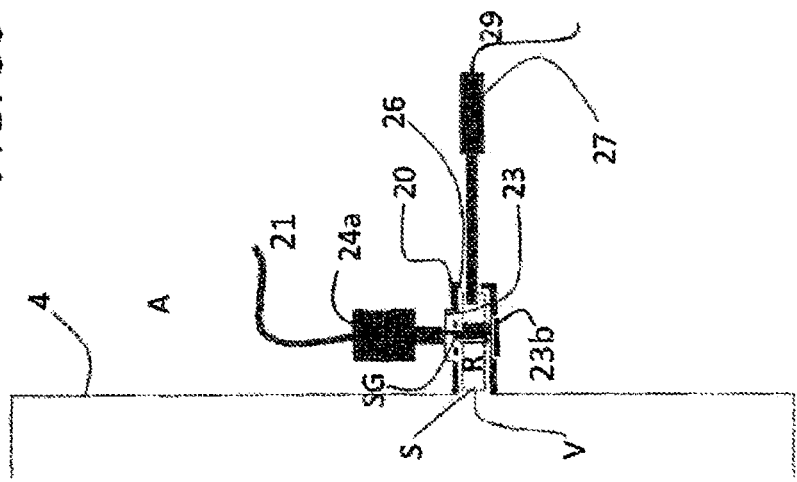
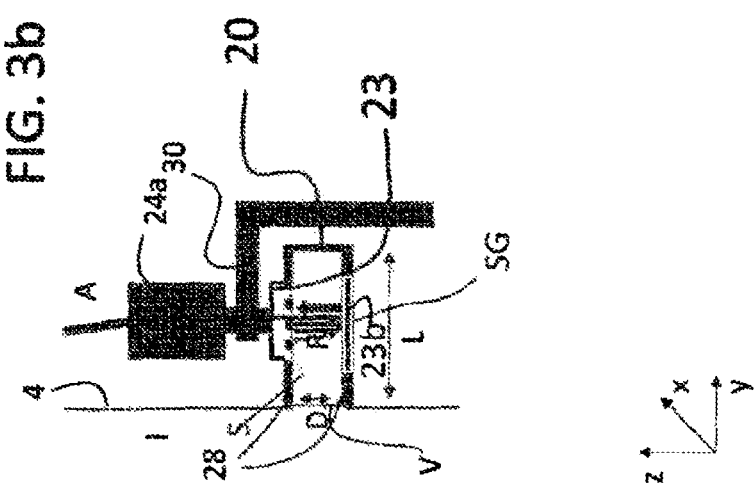
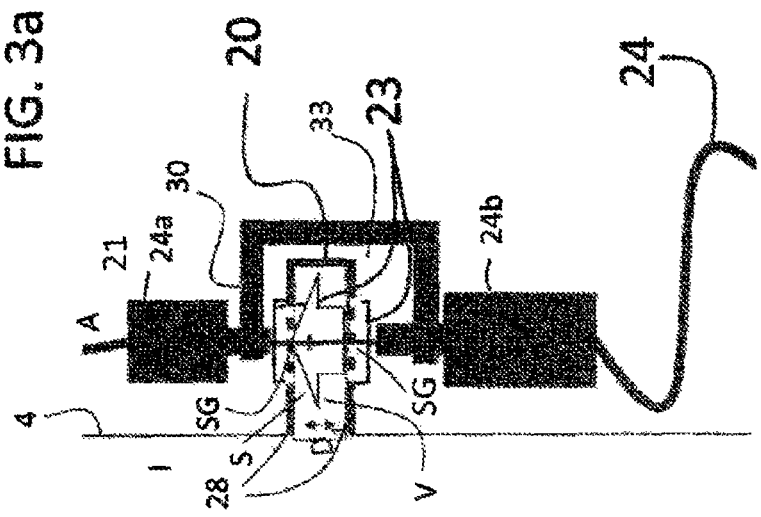

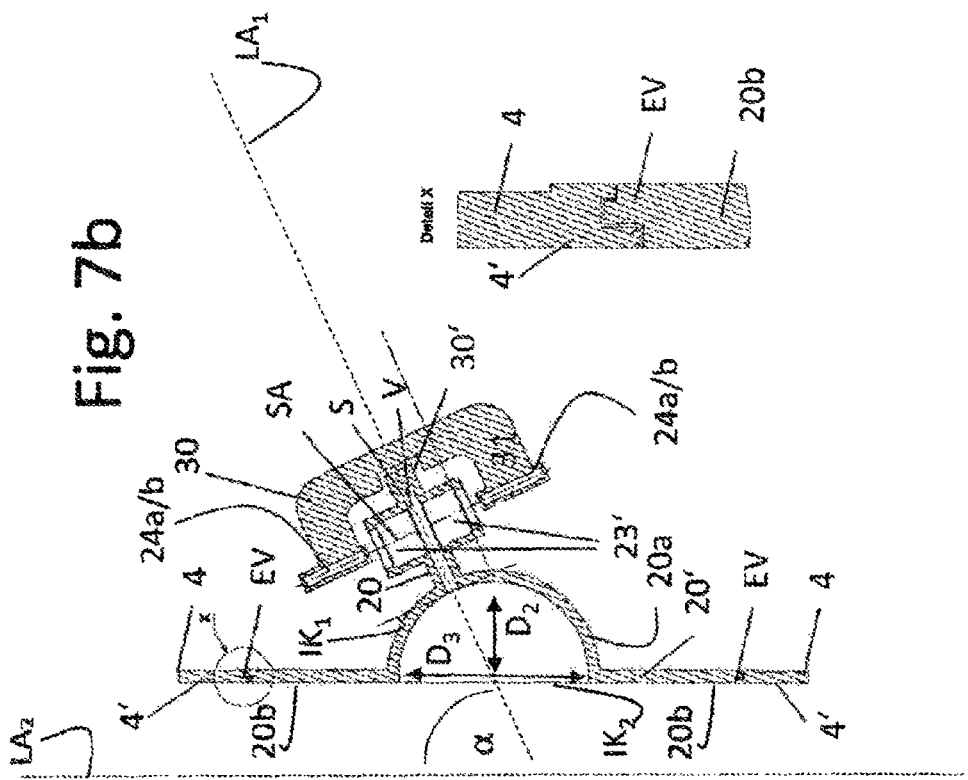
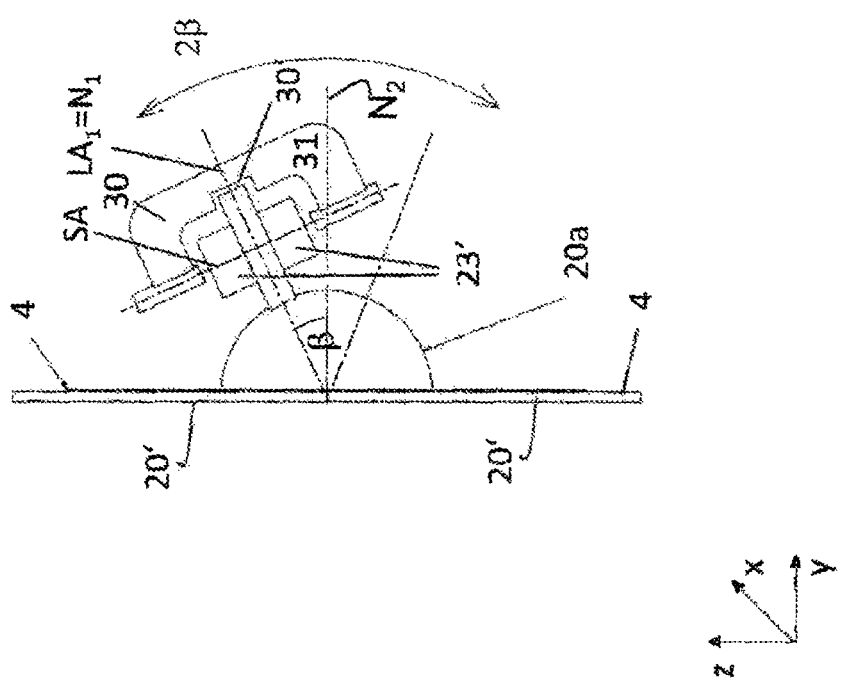

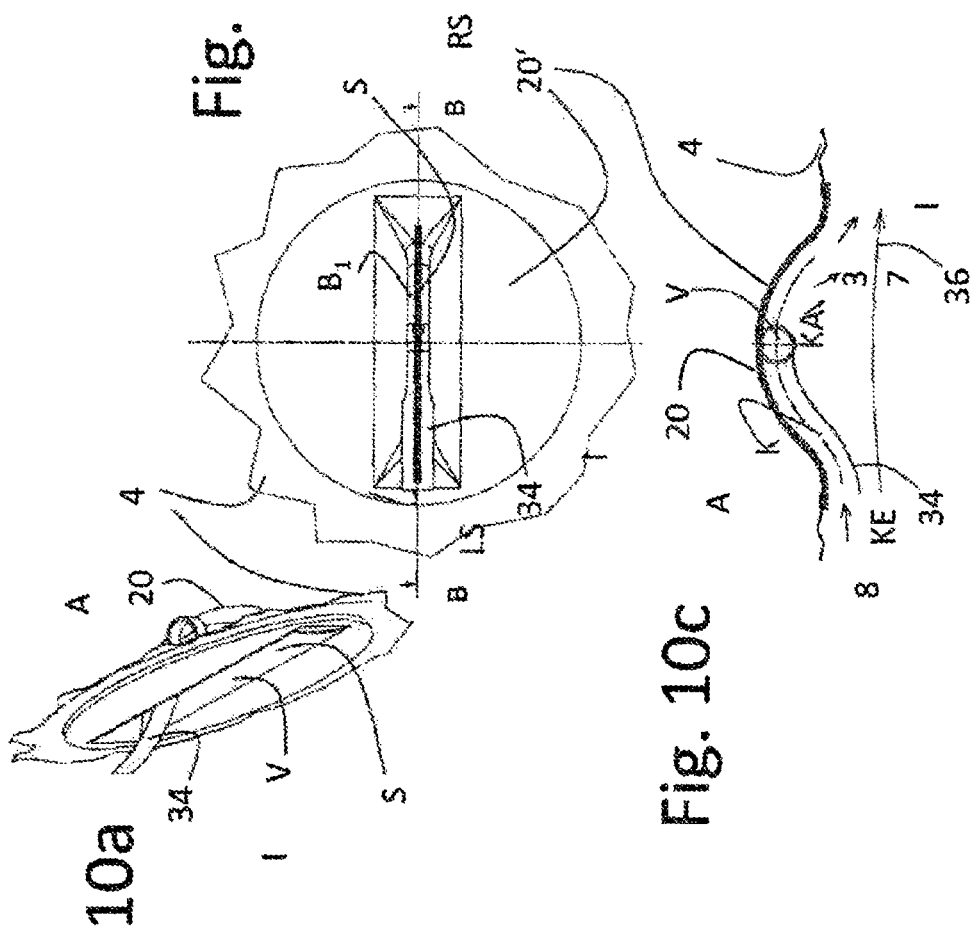

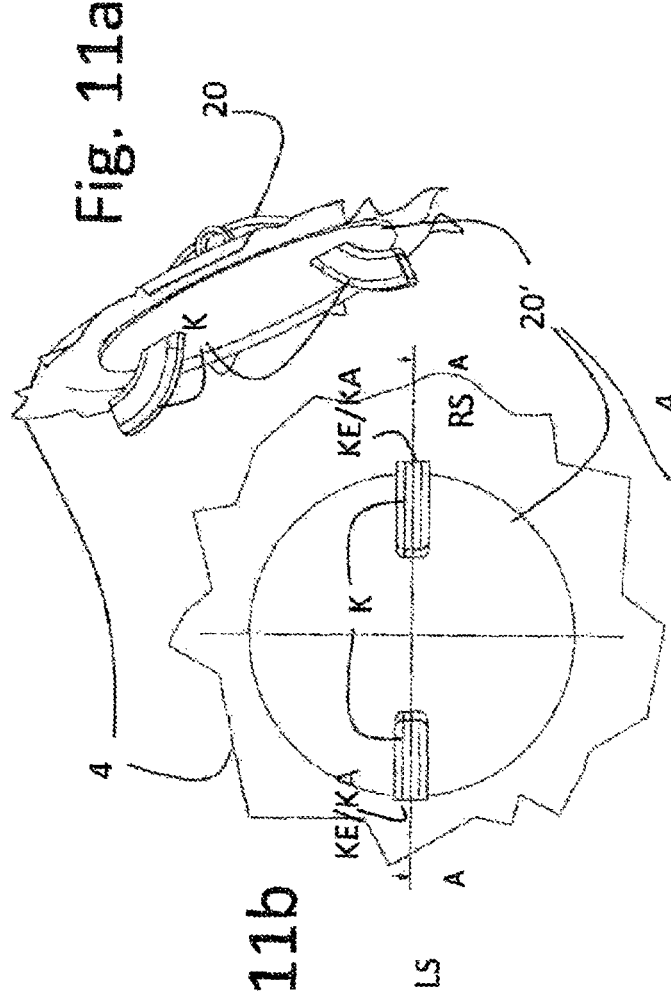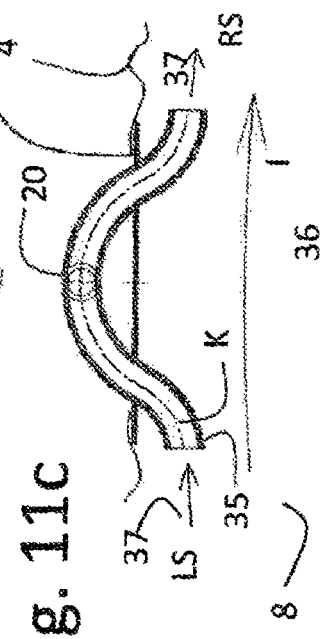

CONTAINER HAVING WALL PROTRUSION AND SENSOR REGION

CROSS REFERENCE TO RELATED APPLICATIONS

This is the U.S. National Stage of International Application No. PCT/EP2018/073412, filed Aug. 31, 2018, which in turn claims the benefit of German Patent Application No. 10 2017 010 629.0, filed Nov. 16, 2017. The prior applications are incorporated herein in their entirety.

DESCRIPTION

The invention relates to a container comprising a wall protrusion, along with a wall protrusion element comprising a wall protrusion for attaching, in particular by means of a sensor attaching device, one or more sensors, preferably an optical sensor as a means for carrying out an optical method. One or more sensors can be used to sense one or more variables or parameters, preferably an optical variable. With the assistance of random or continuous sensing or determination of variables, monitoring, in particular continuous monitoring via a biological and/or chemical and/or biochemical process in one or more media, can be carried out.

Furthermore, the invention relates to a sensor attaching device that can be attached to a container and removed from a container as a means for attaching or fixing or mounting or fastening a sensor, several sensors, a sensor element or a light source, in particular a light conductor, relative to the container and the wall section. A light source can comprise a laser, a diode, a Globar, a Nernst lamp, an arc lamp, an incandescent lamp, a phosphor, a light-emitting diode (LED) and/or any other device emitting light.

The invention can in particular be used in one or more of the following fields: biotechnology, food technology, beverage technology, chemical industry, chemical research, laboratory equipment, medical technology, process chemistry, technical chemistry. The following one or more processes can take place within a container: chemical, biological and/or biochemical processes, in particular fermentation, distillation, purification, decomposition, aerobic processes, anaerobic processes.

Up to now, chemical, biological and/or biochemical processes that take place, for example, within a container of a bioreactor or a fermenter or a food container are monitored such that a variable and/or process stage is determined based on the regular taking of a sample. In doing so, the analysis is to be as representative as possible of the content of a container. Typical variables determined for the conventional monitoring of a process include, for example, the amount of dry substance or organic dry substance, the pH value, the concentration of volatile fatty acids or the ratio of the concentration of volatile fatty acids to the buffer capacity, along with the concentration of trace elements, ammonia, acids, bases, proteins, lipids or other substances.

The dry substance or organic dry substance, for example, represents an indirect measurement of other measured variables or parameters, such as a nitrogen, protein and/or trace element concentration. The ratio of the concentration of volatile fatty acids to the buffer capacity provides information regarding the stage of a process, for example during fermentation. The concentration of volatile fatty acids, such as acetic acid or propionic acid, also provides information regarding the stage of a process because volatile fatty acids are often intermediate products in processes, such as biogas processes. If concentrations are too high, volatile fatty acids can have an inhibitory effect on process biology, for example. As a rule, different methods are used to determine the presence and concentration of fatty acids. Individual fatty acids can be determined by chromatography, for example. The concentration of proteins, lipids and/or other substances, such as ammonia, can also serve as an indicator of the stage of a process and can be determined, for example, by chromatography.

Typically, the determination of variables takes place by a suitable analytical method outside the container, for example by weighing, chromatography, and/or electrochemistry. For this purpose, samples are typically taken from the container and examined in an analysis laboratory. Often, such samples are even sent by mail to an analysis laboratory if no on-site analysis can be performed.

The present invention is based on the object of providing an improved container for monitoring variables of the content or the contained medium. This object is achieved by the independent claims. The subject matters of the dependent claims represent preferred embodiments.

The invention relates to a container with at least one wall protrusion for attaching or receiving or mounting or fixing at least one sensor, in particular an optical sensor or a detector, from an outer side of the container for measuring or sensing at least one measured variable or a parameter to be measured or detected, in particular a physical and/or chemical and/or biological variable of one or more medium(s) contained in a container interior, in particular a biological medium, wherein the wall protrusion is arranged on a container wall of the container and is designed to at least partly surround the container interior and the medium, in particular a sample volume, preferably filled with part of the medium, and wherein the wall protrusion has at least one sensor region, in particular comprising an optical element, for example a window, a prism, a pinhole and/or a diffusely reflecting and/or scattering surface and/or an access point, which is/are designed to allow the measured variable, for example the physical and/or chemical and/or biological variable, to be sensed through the sensor region by means of the sensor, in particular without taking a sample. Preferably, the sensing of the variable is carried out in such a manner that there is no physical contact or touching contact between the sensor and the medium. Alternatively, however, there can also be a touching contact between the sensor and the medium.

The term of a "measured variable" or "variable" has substantially the same meaning as the term of a "parameter," in particular a "parameter to be measured." A variable or measured variable can include a physical and/or a chemical and/or a biological variable.

In the following, physical variables of the medium which can be sensed or measured or detected are understood in particular to be concentration(s) of one or more substances, pressure and/or partial pressure of gases (for example, oxygen, carbon dioxide), concentration of a gas dissolved in a liquid, moisture, number of particles, turbidity, temperature, pH value, electromagnetic radiation, fluorescence, electrical conductivity, capacitive resistance and/or electrical resistance. A physical measured variable can also be or relate to a number, density and/or size of one or more biological cells.

For example, a chemical and/or biological measured variable can be or relate to the amount and/or concentration of a nutrient, such as glucose; or of a titer, such as protein; or of a metabolite, such as lactate. However, no clear distinction is made between the definitions of physical, chemical and biological variables, which is why, in cases of doubt, a biological variable can also correspond to a physical and, in particular, a chemical variable. Particularly preferably, measured variables can include variables that can be determined by optical and/or electrical methods.

The wall protrusion is designed to partly surround a part of the container interior of the container, in particular the sample volume and preferably a slit-shaped sample volume. The sample volume is accordingly a part of the container interior that is in contact with the rest of the container interior of the container. The sample volume is located on the container inner side but, in contrast to the rest of the container interior, it protrudes with the wall protrusion in the direction of the outer side. In other words, there is a connection between the sample volume, which is at least partly surrounded by the wall protrusion, and the rest of the container interior of the container so that a medium in the container interior of the container can also flow into the sample volume. In particular, there is a fluid connection between the sample volume and the rest of the container interior of the container. Stirring or mixing, for example, is a particularly preferred method of preventing the medium, once it has entered the sample volume, from remaining or standing there permanently. In other words, the medium in the sample volume can be continuously or temporarily or sporadically exchanged or replaced by medium from the rest of the container interior by means of mixing. In particular, a sample volume is defined by a slit-like volume or by a slit.

Generally, a sensor that can be attached to or relative to the wall protrusion of the container can include any sensor or detector designed to sense measured variables, for example physical and/or chemical and/or biological variables, of a medium within the container. The sensor can in particular be an optical sensor if a sensor region represents or comprises an optical access or an optical element, in particular a window, a prism, a pinhole and/or a diffusely reflecting and/or scattering surface to the container interior from the outside; i.e., the sensor region is substantially transparent to light of at least one spectral range or at least partly translucent. If the sensor region and/or wall protrusion includes an access in the form of an opening or hole, a sensor can also include a pH sensor that must be in contact with the medium in the container interior in order to sense a pH value. One such sensor is in particular a pH electrode. Generally, the at least one pH sensor can be attached to the wall protrusion continuously or only sporadically or temporarily.

In particular, the container can be designed to form a closed system at least temporarily. It is therefore preferable that the form of the attachment of the sensor to the wall protrusion is suitable for making possible a container that is substantially impervious or impermeable or sealed with respect to the medium inside the container. In other words, the contact point between a container wall and a wall protrusion or wall protrusion element as well as between a sensor and a possible opening is preferably tight such that material exchange between the inner side and the outer side can be substantially prevented.

Variables for monitoring a process, which can be directly or indirectly sensed or recorded by means of a sensor, include optical variables, in particular absorbance, intensity of light scattering, Raman scattering, absorption, fluorescence as well as temperature, particle density, pH value, concentration of volatile fatty acids or the ratio of the concentration of volatile fatty acids to buffer capacity as well as the concentration of trace elements, ammonia, acids, bases, proteins, lipids or other substances, for example dissolved gases.

Through the container, the monitoring of variables can be carried out randomly or sporadically or continuously from the outside, without the need to sample the content of the container. Therefore, the risk of contamination from outside during the collection of a sample by a sampling device, such as a pipette or syringe, and/or by the person collecting the sample is avoided or at least reduced.

It is particularly advantageous that, in most cases, the use of the container substantially eliminates the need to open the container to take a sample, as is required for conventional process monitoring in most cases. This reduces the susceptibility to process disruptions since, for example, a temperature and/or a pressure and/or a gas atmosphere and/or a sensitive and/or unstable material and/or an exposure condition can be affected by opening. For example, a process that requires anaerobic conditions can be disrupted by contact with oxygen from outside. A light-sensitive process can also be disrupted by the opening of the container and the resulting incident light. This circumstance can make sporadic monitoring of a process more difficult and even make continuous monitoring from outside impossible.

In particular, the container or the wall protrusion of the container and in particular a sensor attaching device allows that an exact alignment of electromagnetic radiation or light, for example of excitation radiation or sample radiation, through a medium, along with an exact alignment of a detection channel can be guaranteed. This leads to the fact that reproducible and comparable results can be achieved in a reliable manner.

In addition, the container allows the monitoring of a sample volume inside the container from the outside to be particularly representative. By avoiding sampling, for example, drying out, oxidation, denaturation and/or degradation of the sample material can be reduced or even prevented. It can also be possible to dispense with the need to transport or dispatch a sample to an analysis laboratory, which can save time between collection and analysis, which would be particularly advantageous in the case of the instantaneous monitoring and/or regulation and/or control of the process. This is particularly advantageous if the process within the sample taken would be inhibited or even suppressed by the extraction, and/or if the sample would change in relation to the medium within the container. In order to "freeze" a variable so that it does not change in the sample material compared to the remaining medium in the container at the time of sampling, a sample taken for conventional process monitoring is often frozen. This regularly results in the denaturation and/or degradation of sensitive components of the sample. In particular, the container makes it possible to avoid freezing a sample and its consequences.

In addition, since the taking of sample material or sample medium can be avoided, there is no danger of confusion between samples taken or sample containers taken at different times and/or from different containers.

The effects mentioned can be particularly advantageous if a particularly expensive and/or rare educt and/or product is present in the container. Contamination and/or disruption of a process and/or faulty control and/or faulty regulation can have a fatal effect on the quality of the content, in particular the medium in the container. Furthermore, if monitoring is preferably continuous or at least temporary, there is the possibility that a process can be controlled and/or regulated. In other words, when observing unfavorable process operations or parameter changes, it is substantially possible to take immediate or timely action, for example by adjusting variables, which can prevent valuable products and/or educts from degrading and/or denaturing.

Based on a determination of variables, processes can therefore not only be monitored but also controlled and/or regulated by adding and/or removing substances and/or changing variables or parameters, such as temperature and/or pressure.

According to one aspect, the wall protrusion extends along a longitudinal axis of the wall protrusion, which encloses an angle α of approximately 30° to approximately 150°, in particular of approximately 45° to approximately 135°, with a longitudinal axis of the container and/or a contour line of the container wall of the container. Particularly preferably, the longitudinal axis encloses an angle β of approximately −45° to approximately 45° with a normal to an imaginary contour line for defining the sample volume. In particular, the longitudinal axis encloses an angle β of approximately −45° to approximately 45° with a normal to a longitudinal axis of the container. In particular, a width axis of the wall protrusion encloses an angle γ of approximately −45° to approximately 45° with a width axis of the container.

In other words, the longitudinal axis of the wall protrusion can be inclined "upward" or "downward" with respect to the longitudinal axis of a container. This inclination can be an angle of approximately −45° to approximately 45°, wherein said angle β is between the longitudinal axis of the wall protrusion and a normal or perpendicular to the longitudinal axis of the container. In this case, the normal or perpendicular corresponds to an imaginary contour line of the normal or perpendicular to the longitudinal axis of the container. The angle β here is equal to the value resulting from 90°- α. The angle β can also result from a bulge in the container wall or bag film. This can be the case in particular if a filled single-use bag has a bulbous shape; that is, it has a larger cross-section in a lower area than in an upper area. Then, the medium can deform the container wall in such a manner that the wall protrusion is inclined or pushed "upward." The angle β between the longitudinal axis of the wall protrusion and a normal or perpendicular to the longitudinal axis of the container would then be unequal to 0°, in particular greater than 0° and less than 45°, assuming positive angles for an "upward" inclination of the wall protrusion and negative angles for a "downward" inclination of the wall protrusion.

In other words, the wall protrusion can also be inclined in relation to the width axis of a container. In particular, a width axis of the container can enclose an angle of approximately −45° to approximately 45° with a width axis of the wall protrusion or slit.

An angle γ of approximately −45° to approximately 45° facilitates the material flow of the medium into or through the sample volume of the wall protrusion. On the other hand, an inclination of the wall protrusion in relation to the longitudinal axis of the container can facilitate the attachment of a sensor device. The angle γ of approximately −45° to approximately 45° allows the flow to the port to be optimized.

The advantage of an inclined arrangement of the wall protrusion is that an attaching device for attaching optical elements is particularly easy to attach and/or arrange.

According to one aspect, the container or at least elements of the container can be sterilized. This has the advantage that a medium that is to be filled into the container is not contaminated, for example by unwanted or harmful bioorganisms.

According to one aspect, the container includes a stirring element designed to substantially mix the medium or material inside the container or on the container inner side.

An optional mixing or stirring of the container content can be advantageous for a particularly representative medium within a sample volume that is at least partly surrounded by the wall protrusion. In this case, the sample volume is the volume that is at least partly and in particular substantially surrounded by the container inner side surface of the wall protrusion, i.e., by the surface of the wall protrusion on the container inner side of the container. The sample volume is preferably defined by a slit. Mixing can, for example, allow a process to run as homogeneously as possible within a container and/or allow a part of the medium, for example from the bottom and/or from a central section of the container, to reach the area of the sample volume. Preferably, it is possible to avoid a medium standing within the sample volume, in particular within the slit, or substantially not being in exchange with the rest of the medium.

According to one aspect, the sensor region or the wall protrusion or an optical element, in particular a window, is designed so that the variable, for example the physical and/or chemical and/or biological variable, can be sensed by means of an optical method, in particular optical spectroscopy.

An optical procedure or an optical method is an analytical method and can be carried out or applied with the assistance of an optical sensor. An optical method can preferably include optical spectroscopy. In particular, an optical method can include, for example: optical imaging, microscopy, confocal microscopy, Raman spectroscopy, infrared spectroscopy, light scattering, UV/Vis spectroscopy, laser spectroscopy, fluorescence spectroscopy, terahertz spectroscopy, ellipsometry, refractometry, surface plasmon resonance spectroscopy, and/or, in general, molecular spectroscopy. An optical method can also be used to determine, for example, an oxygen concentration or a concentration of other gases (dissolved in a liquid). Alternatively or additionally, other optical methods for the determination of variables can also be considered.

Optical spectroscopy, for example molecular spectroscopy, such as infrared spectroscopy, can quantitatively and substantially non-invasively provide a direct indication of an essential molecular composition of the medium, or at least give an indication of the presence of substances. Infrared radiation, i.e., electromagnetic radiation in a spectral range which at least partly comprises an infrared spectrum, which infrared radiation is transmitted for example in or through a medium of a sample volume, can excite molecules contained therein to oscillate such that certain wavelengths are at least partly absorbed by the sample depending on the composition of the medium. On the basis of individual absorbed wavelengths or a pattern of absorbed wavelengths or wavelength ranges comprising several absorbed wavelengths, molecular compounds can be identified qualitatively and in particular quantitatively, without destroying the affected molecules. In this manner, concentrations of, for example, molecular components of a medium can be determined directly. It is therefore possible to dispense with indirect and, in particular, faulty methods. Thus, an optical method can, for example, substantially replace a method in which a dry substance is weighed in order to determine the concentration of a substance.

Furthermore, an optical method, in particular a substantially non-invasive optical spectroscopy, is suitable for the permanent or continuous monitoring of variables since the condition of the medium or the process stage in which the medium is located is substantially not affected by monitoring from outside. In addition, as a rule, a change in the variable or process or a procedure can be followed or monitored instantaneously. In this manner, a measure can be taken immediately as a consequence of an observed change in order to control and/or regulate the process. For example, an increasing scattering of light can indicate that a substance unintentionally precipitates into a solid phase and forms particles, whereupon a substance that can prevent particle formation can be added immediately as a countermeasure.

According to one aspect, the wall protrusion comprises two protrusion walls that have a protrusion length and are substantially parallel to one another and spaced apart from one another by a sample layer thickness, and the protrusion length is at least approximately twice the sample layer thickness such that the wall protrusion substantially surrounds a slit-shaped volume or the wall protrusion is slit-shaped or in the form of a slit, wherein at least one of the protrusion walls preferably comprises the sensor region in each case and in particular an optical element, preferably a window. In other words, one protrusion wall of a wall protrusion or several protrusion walls can each comprise or even represent one sensor region. In particular, a protrusion wall of a wall protrusion or several protrusion walls can each comprise or even represent an optical element, preferably a window.

In other words, the wall protrusion can at least partly surround a slit-like volume. Two protrusion walls that are substantially parallel to each other and are spaced apart by a sample layer thickness can ensure, at a constant distance and in particular with a stable and substantially rigid construction, that a large number of measurements can be carried out under the same conditions since the sample layer thickness and thus the volume examined does not change substantially. This is particularly advantageous for calibration measurements since the same sample layer thickness is available for each individual measurement, and changes in the measurement results therefore do not have to be attributed to changes in the sample layer thickness. This allows particularly reliable and precise calibration measurements to be made.

The pronounced protrusion length of the wall protrusion can also facilitate the attachment or fastening or fixation or mounting of light sources, sensors and/or a sensor attaching device since sufficient space can thus be provided for positioning or arranging the sensors on the wall protrusion. The protrusion walls of a wall protrusion can each comprise a sensor region, in particular each an optical element, in particular a window, which is substantially transparent to a wavelength range. Preferably, both sensor regions are also aligned in parallel to each other. In particular, the sensor regions are designed to provide or facilitate a defined and stable beam path into or through part of the medium or sample volume. However, it is also possible that only one sensor region is comprised by a wall protrusion, in particular for a reflective beam path arrangement. Alternatively, two substantially opposite protrusion walls can also be non-parallel.

According to one aspect, the wall protrusion comprises a diffusely reflecting or scattering surface, for example a white surface, and/or a reflective element, for example a mirror. The at least one sensor region comprises the optical element, in particular the window, and the wall protrusion is designed so that the measured variable, in particular the physical and/or chemical and/or biological variable, can be sensed by means of a sensor device, which preferably comprises an optical fiber, through a reflective beam path arrangement, for example a reflective optical arrangement. In other words, the wall protrusion comprises a reflective element and/or a reflective optical arrangement. For example, a reflective element can be a mirror on which light is substantially reflected back in the direction of the optical element, in particular the window and the sensor. In this manner, for example, an optical fiber or a light conductor or a light source can couple or emit a light through the sensor region, in particular the optical element, preferably the window, into a container interior and a reflective beam path arrangement, which is then reflected and/or scattered back at least in part by a reflective and/or a scattering element and emerges or is propagated out of the container interior through the sensor region and is collected or sensed by the same light conductor or another light conductor.

The combination of transmission through the medium and reflection at the mirror and/or a diffusely reflecting and/or scattering surface is called transflection. In other words, one part of a light beam is reflected/scattered on a reflective and/or scattering surface, while another part of the light beam passes through a transmissive surface. This can be the case if a surface has transmissive and reflective and/or scattering properties. An example of such a surface is a beam splitter. Transflection also occurs when one part of a beam hits a reflective and/or scattering surface, while another part of the beam hits and passes through a transmissive surface. Such a combination of a transmission and a reflection corresponds to a "transflective beam path arrangement."

This also includes the case where a wall protrusion comprises two optical elements, in particular two windows, and a diffusely scattering surface and/or a reflector and/or a mirror is or can be arranged in front of or behind one of the optical elements. In another case, one of the two optical elements, for example a window, can be replaced by a diffusely scattering surface and/or a reflector and/or a mirror. In general, optical elements can serve simultaneously as walls of the wall protrusion, or they can be and/or are inserted into a holder in front of or behind a sensor region.

A diffusely reflecting and/or scattering surface is characterized by the fact that it substantially diffusely reflects and/or scatters light. A diffusely reflecting and/or scattering surface can be, for example, a white surface and can comprise a diffusely reflecting and/or scattering material, for example a ceramic and/or a steel plate. If a light hits the diffusely reflecting and/or scattering surface, it is (back) scattered diffusely, i.e., at different angles. At least a part of the light is scattered at such an angle that it passes through the optical element, in particular the window, back outside; that is, it passes the optical element twice.

According to one aspect, the wall protrusion on the container inner side comprises a mirror or reflector that is designed to sense the measured variable, in particular the physical and/or chemical and/or biological variable, by means of a reflective beam path arrangement.

A reflective beam path arrangement usually only requires the provision of a sensor region, preferably comprising an optical element, in particular representing a window or an optical element, and under certain circumstances a mirror or a reflector and/or a reflecting or scattering element or medium on the container inner side of the wall protrusion, which reflect or scatter the incident light back against the direction of incidence. In this manner, the light, which has previously traveled a distance on the container inner side of the wall protrusion, can emerge again through the same sensor region and can be captured or sensed by a sensor or a light conductor, or coupled into a sensor.

For example, a light, in particular a laser light, can be radiated through the sensor region into the part of the container interior in the area of the wall protrusion, where it is scattered, for example, by the medium contained therein and/or by particles, for example mesoscopic and/or nanoscopic particles of the medium. The scattering could include, for example, a Mie, a Raileigh, a Raman or any other light scattering. This can be the case in particular with Raman scattering and/or with static or dynamic light scattering. The scattered light can at least partly exit the container interior again through the one sensor region or alternatively through several sensor regions and is sensed on the outside by a sensor, for example. Such a sensor, in particular an optical sensor, can for example comprise a spectrometer, in particular a Raman spectrometer and/or a CCD camera and/or a photomultiplier.

Alternatively or additionally, the incident light can also be scattered back or reflected by a mirror or a substantially reflective optical element on the opposite container inner side of the sensor region so that it exits the container interior through one or more sensor regions and can be sensed by a sensor on the outside. In other words, light can propagate substantially from a first direction through a sensor region, in particular through an optical element, preferably a window, into a container interior or into a sample volume of a wall protrusion, can be scattered or reflected at least partly on the container inner side substantially against the first direction or back so that at least a part of the light exits the container interior again through the sensor region through which it entered. After exiting, the light can be at least partly sensed or captured by a light conductor.

The effective path length of a reflective beam path arrangement, within which incident light can interact with the medium, for example the molecules contained in the medium, corresponds to substantially twice the sample layer thickness or substantially twice the path length between the sensor region and the mirror or between the sensor region and the scattering medium, wherein a scattering medium can be, for example, a particle or nanoparticle contained in the medium or droplets of an emulsion.

It is also possible that only a light that passes from the container inner side through a sensor region to the outside is sensed by a sensor. For example, a fluorescence can be sensed. This means that a medium or components of a medium in the container interior at least partly fluoresce and at least partly emit light that leaves the container interior through a sensor region, for example a window. A light conductor or a sensor or an element of a sensor device can then capture and/or sense and/or detect and/or record the photons or the light emerging from the container interior.

According to one aspect, the wall protrusion comprises a shutter or an aperture that is designed to reduce or prevent, at least temporarily, the entry of light substantially into the container interior through a sensor region, in particular an optical element, preferably a window. The shutter or aperture can be attached from the outside or on the container inner side relative to the wall protrusion. Preferably, the shutter can be actuated or operated from the outside in such a manner that light incident on the container inner side can be monitored, regulated, controlled or modified.

It can be advantageous that a shutter or an aperture at least temporarily substantially reduces or prevents the entry and, for example, the interaction of the medium in the container interior with light. The aperture or shutter can substantially completely block the incidence of light of all wavelengths. For example, one step or stage in a process can be sensitive to light, such as UV light and/or visible light, whereas another stage in the process can be insensitive to light. In this case, a shutter can be opened or closed if necessary. The aperture or shutter can also include a filter so that only a spectral range of incident light is substantially blocked. The aforementioned possibilities exist not only for incident light from outside but also for light that could be emitted to the outside and that is generated, for example, on the container inner side and/or propagated through parts of the container interior and/or emitted by a medium in the container interior.

Depending on whether a shutter substantially closes off or blocks or seals the sensor region, in particular the window, against the incidence of all light or parts or frequency ranges of light, or whether a shutter is at least partly in an open position that is designed to allow at least partial light or at least frequency ranges of light to propagate through the sensor region from inside or from the container inner side to the outside and/or from the outside to the inside or to the container inner side, there can consequently be a decision of whether a measured variable, in particular a physical and/or chemical and/or biological variable, is to or is not to be sensed from the outside by means of a sensor through the sensor region. For example, a measurement can be recorded while a shutter is in an open position. If a shutter or an aperture is substantially in a position that, at least in parts, prevents at least parts of a light from propagating from the outside to the inside and/or from the inside to the outside, a measurement or sensing of variables can be paused or stopped.

According to one aspect, the wall protrusion comprises at least two sensor regions, in particular two optical elements and preferably two windows, particularly preferably two windows aligned or arranged in parallel to one another, wherein the wall protrusion is designed or the two sensor regions are designed so that the variable can be sensed through a transmissive beam path arrangement by means of a sensor device, which preferably comprises an optical fiber. Alternatively, two optical elements, preferably two windows, can also be aligned or arranged substantially not in parallel to each other. It is possible that the sensor regions each comprise or represent an optical element, in particular a window.

A transmissive beam path arrangement can, for example, allow light or electromagnetic radiation from a light source, for example a laser beam, to be beamed or transmitted from outside through a first sensor region, in particular through an optical element, preferably a window, into the container interior or onto the container inner side of the wall protrusion. The light can pass at least partly through the medium of the sample volume or sample volume layer thickness and interact at least partly with the medium before it passes through a second sensor region, in particular an optical element, preferably a window, and is sensed by a detector. For example, absorption can be determined or sensed by means of infrared spectroscopy and/or UV/Vis spectroscopy. Absorption can in turn be a measure of the concentration of a substance.

The effective path length of a transmissive beam path arrangement, within which incident light can at least partly interact with the medium, for example with the molecules contained in the medium, substantially corresponds to the sample layer thickness or the path length from the first to the second sensor region.

It is also explicitly possible for a wall protrusion to be designed in such a manner that a transmissive beam path arrangement can optionally be used, for example at the same time or alternately in succession.

According to one aspect, a container comprises a sensor attaching device for attaching the sensor and/or a light source relative to and/or on the wall protrusion.

A sensor attaching device can be in the form of a frame, for example, and can be formed to be preferably rigid. The sensor attaching device allows one or more sensors to be attached and/or fastened and/or mounted and/or fixed relative to the wall protrusion in such a manner that the attached sensor can sense a variable or parameter through a sensor region, in particular through an optical element, preferably a window.

The sensor attaching device can in particular be used to attach and/or fasten and/or mount and/or fix one or more light conductors to the wall protrusion. For example, particularly in the case of a transmissive beam path arrangement, a light conductor can also be attached by means of a sensor attaching device, wherein the light conductor represents a light source and light or electromagnetic radiation radiates through a first sensor region into the container interior of the container, in particular the wall protrusion. In the case of a transmissive beam path arrangement, a sensor and/or a light conductor of a sensor can also be attached to the wall protrusion element by means of a sensor attaching device, wherein the sensor at least partly senses or captures the irradiated light of the light source, for example, through a second sensor region. If the spectrum of the irradiated light is known or sensed and the spectrum of the light which passes through the medium at least partly is sensed, absorption can be determined, for example.

The sensor attaching device can also be used to attach elements other than a light source and/or a light conductor and/or a sensor, such as optical elements, relative to the wall protrusion and the container. The sensor attaching device can also be used or designed to attach and/or fasten and/or mount and/or fix one or more pH sensors relative to the wall protrusion.

According to one aspect, a container comprises a sensor attaching device for attaching the sensor relative to the wall protrusion, which sensor attaching device can be attached to the container to the wall protrusion, in particular reversibly, and can be removed or detached from the container or the wall protrusion. In other words, the sensor attaching device can be attached and removed relative to the wall protrusion as required. For example, attaching a sensor to the sensor attaching device can require the sensor attaching device to be removed or detached from the container.

A sensor attaching device detachable from a container can be used or designed to be attached to and detached from the wall protrusions of different containers. In particular, if the removable sensor attaching device is rigid and the sensor attaching device pre-determines or pre-adjusts or pre-sets and maintains an optical beam path, for example, variables for the media within different containers can be compared directly with each other. For example, a transmission and/or an absorbance and/or an absorption can be used to determine whether the processes taking place within two containers differ from each other and/or whether they take place at different times.

A sensor attaching device detachable from a container can also be used to take a calibration measurement or background measurement before attaching to a wall protrusion of a container. For example, the light from a light source attached to the sensor attaching device can pass through a layer of air substantially relative to the sensor attaching device where, in a position attached to the container, a medium would be positioned relative to the sensor attaching device and would be sensed by means of a sensor attached to the sensor attaching device. Substantially, the spectrum of a light irradiated by a light source, for example light in an infrared spectrum and/or a UV/Vis spectrum, can thus be determined or sensed and/or ascertained. After the sensor attaching device has then been attached to the wall protrusion, or in a position attached relative to the wall protrusion, light with a certain spectrum which has passed through the medium in the container interior of the wall protrusion, or in the sample volume, can be sensed by means of the detector or sensor using the same optical geometry. By means of a mathematical operation, for example by subtraction and/or by division of both spectra, an absorption of light with certain frequencies or frequency ranges by the medium can be ascertained.

Alternatively, the sensor attaching device can also be continuously or at least temporarily fixed or attached to the container or to a wall protrusion element. In particular, a sensor attaching device can be integrated on a container and/or a wall protrusion element and/or be formed integrally or in one piece therewith.

Therefore, according to one aspect, a container alternatively comprises a sensor attaching device fixed to the container for attaching the sensor to the wall protrusion.

A sensor attaching device fixed to the container can be used to easily attach an optical sensor and/or pH electrode relative to the wall protrusion. In particular, a sensor attaching device fixed to the container can be formed or shaped in one piece with a wall protrusion element and/or with the container itself.

According to one aspect, the sensor attaching device comprises at least one receiving device, which is designed to receive an additional optical element, in addition to the optical element serving as a sensor region, in particular as a window, preferably a lens and/or a mirror and/or a prism and/or a pinhole, and/or at least one additional optical element, in particular a pinhole and/or an iris and/or a reflector or a mirror or a reflective element and/or a lens and/or an aperture and/or a filter, for example a notch filter.

A sensor attaching device with an optical element can be used to influence an optical beam path or light path by means of the optical element. For example, a notch filter can block or filter out substantially all or at least part of the incident light from a laser with a certain wavelength or a certain wavelength range, whereas light of a slightly different wavelength can substantially pass through the filter. This can be advantageous if variables are determined by means of Raman spectroscopy. In this case, a so-called Raman shift causes a shift in the wavelength of a scattered light, which is to be sensed separately from the irradiated electromagnetic radiation, whereas the irradiated electromagnetic radiation is substantially filtered out or blocked by means of a notch filter.

The sensor attaching device can, for example, also include receptacles into which optical elements can be inserted, in particular modularly and/or interchangeably and/or reversibly. This allows a beam path to be adapted to the conditions or the method in a particularly flexible and yet reversible manner. Alternatively, the sensor attaching device can also continuously comprise, in addition to the optical element serving as the sensor region, an additional optical element which is, for example, bonded and/or welded and/or screwed to the sensor attaching device.

According to one aspect, the wall protrusion element, in particular the wall protrusion, comprises at least one additional optical element, in particular a pinhole and/or a reflector and/or a filter, for example a notch filter.

According to one aspect, the container is designed to be a component of a disposable bioreactor.

In particular, according to one aspect, the container substantially constitutes a disposable bioreactor such that the wall protrusion is arranged on a container wall of the container, that is, of the disposable bioreactor.

According to one aspect, the container is a disposable container.

A disposable element, such as a disposable container, in particular a disposable bioreactor, has the general advantage that it can be provided in sterile form and does not have to be cleaned or autoclaved again but can be disposed of after use and contamination with content. By using cost-effective materials for the production of disposable bioreactors, processes can be carried out or implemented particularly cost-effectively. All components of a container, in particular of a bioreactor, along with all accessories can be designed as disposable elements. Alternatively, some components of a container, in particular of a bioreactor, and some components of an accessory, can be designed as disposable elements, whereas other components are reusable elements.

In particular, a wall protrusion element with a wall protrusion at least partly made of a plastic and/or a metal, in particular steel, can be attached and/or fixed and/or glued and/or welded to the container wall of a disposable bioreactor. In this manner, the wall protrusion element and the container or disposable bioreactor can be made in several pieces, in particular in two pieces, and connected by a composite material. Alternatively, the wall protrusion element and the container or disposable bioreactor can be made in one piece.

According to one aspect, the container is designed to be a component of a reusable bioreactor.

According to one aspect, the container represents a reusable container, in particular a reusable bioreactor, in such a manner that the wall protrusion is arranged on a container wall of the container, i.e., the reusable bioreactor.

In cases in which a particularly large quantity of a medium, for example more than 500 l, in particular more than 5000 l, is to be processed and/or stored and/or transported in one container, it is advantageous to use a particularly large container, for example a steel tank.

Such containers prove to be particularly cost-effective in reusable applications, for example as reusable bioreactors and/or reusable fermenters and/or reusable mixing systems and/or reusable brew kettles and/or reusable digestion systems.

In particular, a wall protrusion element with a wall protrusion, at least partly formed from a metal, in particular steel, can be attached and/or screwed and/or fixed and/or glued and/or welded relative to and/or to the container wall of a reusable container or reusable bioreactor. In this manner, the wall protrusion element and container or reusable bioreactor can be made in several pieces, in particular two pieces, and connected by a composite material and/or other means. Alternatively, the wall protrusion element and the container or reusable bioreactor can be formed in one piece.

According to one aspect, a wall protrusion element comprising the wall protrusion and optionally a wall bulge, in particular the wall protrusion and/or a wall bulge, comprises at least one access point, which is designed so that in particular a pH value can be sensed through the access point by means of a pH electrode. In this case, the pH electrode can be in physical contact with the sample volume and can determine a variable or parameter of the sample volume. The pH electrode can protrude into the container interior, in particular into the sample volume, and can be in physical contact with a medium. In other words, a wall protrusion element comprises a sensor region. In particular, a wall protrusion and/or an optional wall bulge comprises a sensor region. In this case, the sensor region represents an access point, for example an opening for attaching or mounting or holding a pH electrode.

It can be advantageous, for example, to use an optical method and pH measurement simultaneously for monitoring processes in a complementary manner in order to sense variables as precisely as possible and, in particular, complementary or non-redundant variables and to obtain information regarding the course of a process.

According to one aspect, a container comprises a wall protrusion element, which comprises the wall protrusion and optionally possibly a wall bulge. It is therefore possible that a wall protrusion is arranged on a separate wall protrusion element, which in turn is or can be fastened or attached to a container. In addition, the wall protrusion element can also comprise a wall bulge in addition to the wall protrusion. It is possible that a wall protrusion element can be subsequently attached to a container or can be replaced on a container.

Due to its shape, a wall bulge can give the wall protrusion element increased stability. Furthermore, a wall bulge can offer additional space for an access point and/or an opening and/or a sensor region through which a sensor, for example an optical sensor but in particular a pH sensor, can, for example, come into contact with the container interior or the medium contained in the container interior. For example, a pH electrode can be attached to a wall bulge. In the container interior of the container, the sensor is at least partly protected against, for example, swirling parts or stirring elements due to the wall bulge, depending on how far the wall bulge extends into the container interior.

According to one aspect, a container comprises a wall protrusion element that surrounds the wall protrusion and is formed in one piece with the container. In other words, a container with a wall protrusion element and a wall protrusion can be formed in one piece, for example by means of a casting technique or a 3D printing method.

According to one aspect, a container comprises a wall protrusion element that surrounds the wall protrusion and is formed in several pieces with the container. In other words, the container can comprise a wall protrusion element and, in particular, a wall protrusion, wherein the wall protrusion element has been subsequently attached to the container, for example by means of gluing, welding, screwing, plugging (onto or against) or fusing.

The invention also relates to a wall protrusion element for fastening to a container wall of a container comprising a wall protrusion, in particular also a wall bulge, for attaching the wall protrusion to a container wall of a container, wherein the wall protrusion
- is designed for the attachment of at least one sensor from the outside of the container for the sensing of at least one variable or measured variable or parameter, in particular a physical and/or chemical and/or biological variable, of a medium contained in a container interior;
- is at least partly formed in a manner surrounding the container interior; and
- comprises at least one sensor region, which is designed so that the variable or parameter can be sensed through the sensor region by means of the sensor.

Thus, a wall protrusion element can also be provided for attaching a wall protrusion to a container as a single element, wherein the wall protrusion element comprises the wall protrusion for attaching or receiving at least one sensor or detector, in particular an optical sensor for measuring at least one variable of media contained in a container interior. This can be particularly advantageous if containers are to be retrofitted in such a manner that they are provided with a wall protrusion element along with a wall protrusion. In the separate production of the container wall and the wall protrusion element, both elements can then be joined or attached to each other in a (last) step, preferably in a form-fitting and tight manner.

In a state attached to a container, the wall protrusion at least partly surrounds the container interior, in particular at least partly a sample volume. The wall protrusion preferably comprises at least one sensor region, in particular at least one optical element, preferably a window and/or at least one access point, wherein the sensor region or access point is designed so that the variable can be sensed through the sensor region or access point by means of the sensor, in particular and substantially without taking a sample volume.

The fastening of the wall protrusion element to the container wall can be reversible according to one aspect, which has the advantage that the wall protrusion element can be used for different containers.

However, the fastening of the wall protrusion element to the container wall can also be irreversible according to one aspect, which has the advantage that the wall protrusion element can be formed with a single-use container and can be used once.

According to one aspect, the wall protrusion element can be sterilized or is designed to be sterilized or autoclaved or heated to ultra-high temperatures.

In particular, the wall protrusion element is made of one or more materials that can be sterilized or autoclaved. For example, the wall protrusion element can be made of a steel and/or plastic, in particular a polymer. This has the advantage that the container together with the wall protrusion element can be sterilized before use so that a medium that is filled, for example, into the container interior of the container and that can flow partly into the sample volume partly surrounded by the wall protrusion is in particular not contaminated with microbiological material. Sterilization can be carried out before the first and last use of a disposable container, in particular a disposable bioreactor, or sterilization can be carried out before and after or between each use of a reusable bioreactor.

The invention also relates to a sensor attaching device for attaching or fixing or mounting at least one sensor or one detector or one sensor device or one element of a sensor device relative to or to a sensor region of a wall protrusion of a container from an outer side of the container, wherein the sensor attaching device comprises a receiving device or holder or fixation for receiving or holding or fixing the sensor or detector or sensor device or element of a sensor device for sensing at least one variable or parameter of a medium contained in a container interior of the container; and can be attached by means of a recess or bulge relative to or to the wall protrusion such that at least one section of the wall protrusion and at least one part of the medium, along with a part of the sample volume for sensing or measuring the variable through the sensor region, in particular the optical element, preferably the window, by means of the sensor is positioned within the recess.

A sensor attaching device can, for example, be used universally for the attaching or fixing or mounting of at least one or more sensors or a detector or a sensor device or an element of a sensor device on sensor regions of wall protrusions of several containers. For example, a sensor can be attached or fixed to the sensor attaching device permanently or at least for a period of time, wherein the sensor attaching device is initially attached to a wall protrusion of a first container to sense a variable, in particular a physical and/or chemical and/or biological variable, and after sensing is then attached to a wall protrusion of a second container to sense a variable again. In this manner, a sensor attaching device with a sensor and a measuring system can successively monitor a variable of a series of containers or processes or media.

According to one aspect, the sensor attaching device is designed to attach or fix or fasten or mount at least one optical sensor or detector and/or a light conductor relative to a sensor region in such a manner that the variable can be sensed by means of an optical method, in particular optical spectroscopy.

According to one aspect, the sensor attaching device is designed to arrange light conductors and/or sensors, for example two light conductors or one light conductor and a sensor, relative to each other in such a manner that a transmissive and/or a reflective beam path arrangement exists or arises.

It is particularly advantageous if light conductors and/or sensors are fixed relative to each other on the sensor attaching device in such a manner that a pre-aligned or permanently fixed beam path is provided, and measurements can be carried out under the same conditions or adjustment conditions over a longer period of time. This is particularly advantageous for background measurements and comparisons of measurement data and calibrations. In addition, it can also be possible that such a beam path, in particular a transmissive and/or reflective beam path, is also finely adjustable in such a manner that beam paths can substantially be adapted reversibly.

In the case in which a reflective beam path arrangement is provided or exists, for example, light from a light source can be transmitted or radiated into the medium through a single sensor region, in particular an optical element, preferably a window, for example through a light conductor. At a reflective and/or scattering element, the light in the container interior of the container can then be reflected and/or backscattered, can pass through the sensor region and can be sensed by a detector and/or a light conductor of a detector.

In the case in which a transmissive beam path arrangement exists, light from a light source can, for example, be transmitted or enter the medium through a first sensor region, in particular a first optical element, preferably a first window, for example through a light conductor, and after passing a part of the medium in the container interior of the container, can pass through a second sensor region, in particular a second optical element, preferably a second window, and can be sensed by a detector and/or a light conductor of a detector.

Alternatively, a beam path can be transmissive with respect to one part of the beam or with respect to one part of the cross-sectional area of the light beam and reflective with respect to the other part of the beam. For example, a second sensor region for a transmissive beam path arrangement can be half or partly covered by a mirror so that a part of the beam or a part of the cross-sectional area of the light beam follows a reflective beam path arrangement.

In particular, absorption measurements can be performed by means of a transmissive or a reflective beam path arrangement. The reflective beam path arrangement allows the optical path through the medium to be substantially longer than the transmissive beam path arrangement.

According to one aspect, the sensor attaching device is designed to be arranged or mounted or fixed relative to or to a flow cell or a bypass in such a manner that by means of a sensor attached or mounted or fixed to the sensor attaching device, a (physical and/or chemical and/or biological) variable of a medium flowing or stored or located therein can be sensed or measured through a sensor region, in particular through an optical element, preferably a window of the flow cell.

In particular, the sensor attaching device can be used universally and in modular form in such a manner that the sensor attaching device is designed to be attached or mounted or fixed relative to or to wall protrusions of different containers and/or different flow cells.

In particular, several wall protrusions along with wall protrusion elements are also uniformly formed in such a manner that, for example, wall protrusions on different containers have the same shape and/or have the same shape as a section of a flow cell that has a sensor region, in particular an optical element, preferably a window. In this manner, a universal plug connection can be formed between the sensor attaching device and wall protrusion and/or flow cell. In this case, it can be assumed that a wall protrusion can receive a sensor attaching device. Alternatively, one can assume that a sensor attaching device can receive a wall protrusion or a flow cell.

It is possible that the container with the wall protrusion is substantially not moved relative to or against the wall protrusion during the step of attaching the sensor attaching device, whereas the sensor attaching device is, for example, plugged onto the wall protrusion or attached to the wall protrusion. This is particularly the case or preferred if the container is particularly large and/or heavy and/or is fixed in place. Then, the case can apply that it is assumed that a wall protrusion receives a sensor attaching device. Alternatively, a sensor attaching device is substantially not moved relative to or to the wall protrusion or flow cell or bypass during the attaching step, whereas the container with the wall protrusion or bypass must be moved relative to the sensor attaching device. Then, the case can apply in which a sensor attaching device receives a wall protrusion or a bypass.

It is possible that a sensor is first received by a sensor attaching device, or a sensor is first attached or mounted or fixed to a sensor attaching device, and then the sensor attaching device with the sensor is attached or mounted or fixed relative to or to the wall protrusion.

Alternatively, the sensor attaching device can first be attached or mounted or fixed relative to or to the wall protrusion without a sensor, and then the sensor is received by the sensor attaching device or the sensor is attached or mounted or fixed to the sensor attaching device. In this case, it is also possible that the sensor attaching device is permanently mounted relative to or to the wall protrusion in order to repeatedly receive or mount or fix or attach different or several sensors.

The invention also relates to a method for sensing or measuring or detecting at least one variable, in particular a physical and/or chemical and/or biological variable; or a parameter; or a state of a medium contained in a container interior of a container, comprising the following steps:
    arranging or attaching or providing, in particular by gluing or welding or integrally forming, a wall protrusion on a container wall of the container;
    at least partly surrounding or enclosing the container interior and the medium by the wall protrusion;
    providing or arranging or attaching at least one sensor region, in particular at least one optical element, preferably a window, and/or access point to the wall protrusion;
    attaching from an outer side of the container, in particular by means of a sensor attaching device, at least one sensor or one detector or one sensor device, in particular an optical sensor, relative to at least one wall protrusion; and
    sensing the variable, in particular the physical and/or chemical and/or biological variable of the medium, in particular by means of an optical method, preferably optical spectroscopy, through the sensor region by means of the sensor.

In the context of the present invention, containers are understood to mean in particular containers for mixing, storing and/or transporting, as well as bioreactors or containers as components of bioreactors and fermenters but also vessels, canisters and containers for storing buffer solutions. A bioreactor or fermenter can comprise or represent a container. The container can also be, for example, a mixing tank or mixing container, a storage container, a bottle, a canister or a food tank or food barrel. The container can also be a container in which chemical material is stored, transported and/or processed, or a container can represent a chemical laboratory device, for example a column vessel for column chromatography, a vessel or an element of, for example, a still. Such a container can be designed for one-time use or for reusable use. In particular, a container can be at least partly made of plastic. Alternatively, a container can also be at least partly made of a metal, in particular steel. In addition, a container can be at least partly made of glass.

Containers, such as bioreactors, mixing systems and pellet tanks, are substantially used for receiving, storing and mixing biological media, such as fluids and/or solids and/or gases. Biological media can be provided in containers, such as bags, in particular plastic bags, which can have a volume of several hundred liters. The biological media preferably can be introduced within such a bag into the bioreactor, where they can be stored, tempered and/or mixed. In such a bioreactor, different examinations can be carried out on the biological medium.

In the context of the present invention, liquids, gases, suspensions, dispersions, buffers and/or cell culture broths in particular are regarded as medium or media. Media can also comprise solids, such as powders, pressed pellets, particles, grains, and mixtures thereof. A medium can accordingly comprise different components with the same or different aggregate state, for example an emulsion or a dispersion.

A wall protrusion element can comprise a wall bulge but at least one wall protrusion. The wall protrusion element can be attached to or fixed to or arranged on a container wall or can be designed to be attached to or fixed to or arranged on a container wall. The wall protrusion element forms with the container wall an outer shell, which at least partly surrounds the contained volume or the container inner volume or the container interior of the container, which can be filled with the medium, surrounds it at least partly and in particular completely surrounds or encloses it. It is also possible that the wall protrusion forms a shell with the container wall. The shell or skin or wall formed by the container wall and the wall protrusion element or wall protrusion separates or insulates the container interior, which corresponds to the container inner volume or the container inner side, from an outer side in such a manner that a medium or content located on the container inner side or in the container interior is at least partly substantially shielded or isolated or separated from the outer side.

The volume substantially surrounded by the wall protrusion element, in particular the sample volume, is in contact or medium exchange or fluid exchange with the volume substantially surrounded by the container wall, for example by means of an opening. For example, a slit partly surrounded by the wall protrusion opens toward the container interior. Alternatively, the volume substantially surrounded by the wall protrusion element, in particular the sample volume, can be temporarily isolated from the volume substantially surrounded by the container wall, for example by means of a shutter or flap that can be operated from the outside.

The wall protrusion can comprise two protrusion walls that are substantially parallel to each other. A protrusion wall can comprise a sensor region, resulting in the protrusion wall being divided into a sensor region section that substantially represents the sensor region and a wall section that substantially represents a wall that does not comprise the sensor region.

The wall protrusion can, for example, be substantially and at least partly made of a plastic, glass or metal. The wall protrusion furthermore comprises one or more sensor regions, wherein a sensor region represents an access point, in particular an optical access point for an optical sensor, preferably an optical element, such as a window, a prism, a pinhole and/or a diffusely reflecting and/or scattering surface. In other words, a sensor region can initially be generally understood as an access point. In particular, a sensor region represents an access point for an optical sensor. Preferably, a sensor region, in particular an optical element, preferably a window, is characterized in that it is substantially or at least partly transparent to a spectral range or wavelength range of an electromagnetic radiation. In particular, a sensor region is designed to tightly separate the container inner side or the container inner volume, which corresponds to the container interior, from the outer side. Alternatively, a sensor region can also comprise or represent an opening between the container inner side and the outer side.

For example, a sensor region can be formed substantially or at least partly of a plastic or glass or other material that is substantially translucent or transparent to a spectral range. Preferably, a sensor region is transparent or translucent to a light of a broad, in particular at least partly visible, wavelength spectrum or frequency spectrum. However, the sensor region can alternatively or additionally also be transparent to light with wavelengths and/or a wavelength range in the invisible wavelength spectrum, for example to infrared and/or ultraviolet light. For example, a sensor region made of silicon would be substantially transparent to light of infrared wavelengths but not to light of visible wavelengths. For example, a sensor region made of glass would be transparent to visible light but not to parts of ultraviolet light. Therefore, the wall protrusion can be made of plastic, for example, and can comprise a sensor region made of glass, in particular quartz glass. Alternatively, however, the wall protrusion and the sensor region can also be made entirely of glass so that the material of the wall protrusion does not differ from the material of the sensor region.

In other words, a sensor region, in particular an optical element, preferably a window, for example, can be at least partly transparent to light in the infrared, visible and/or ultraviolet spectral range, in particular to thermal radiation.

The term "visible wavelength range" refers to those wavelengths of light that are substantially visible to a human being, in particular between approximately 380 nm and 780 nm. The term "invisible wavelength range" refers to those wavelengths of light that are substantially invisible to a human being, for example, wavelengths shorter than approximately 380 nm or longer than 780 nm. The term "light" used here is not limited to the visible spectral range but refers to electromagnetic radiation in general.

Therefore, according to one aspect, the wall protrusion comprises at least one sensor region, which is designed in particular to be replaced on the wall protrusion.

This is particularly advantageous if a sensor region is or becomes damaged so that the damaged sensor region can be replaced by a new sensor region, or if a measurement would require transparency of a sensor region in another predetermined wavelength range compared to a previous different measurement.

According to one aspect, a wall protrusion comprises protrusion walls that, at least in sections, have an extension that protrude in the direction of the container inner side, i.e., into the container or into the interior of the container. The extensions protrude into the container interior and protrude from the inner side of the wall protrusion. Accordingly, a wall protrusion comprises protrusion walls that protrude onto the container inner side or into the container interior. Alternatively, a protrusion from the container wall can also protrude in the direction of the inner side.

By means of an extension of a protrusion wall, a material flow or a flow of the medium, in particular triggered by stirring or agitating the medium within the container, can be influenced, in particular slowed down and/or deflected, preferably on the inner side of the container wall. The flow into the sample volume of the slit-shaped wall protrusion can thus be reduced or calmed. In particular, a medium within the sample volume can substantially come to a standstill although a stirring device is agitating most of the medium within the container.

The material of the wall protrusion can be designed in such a manner that ambient light is shielded or weakened. This can be done, for example, for the UV-Vis range by choosing a dark material. The shielding can be influenced by increasing the material wall strength.

A container can be a component of a bioreactor and/or of a fermenter. For example, a container can also be a component of a food tank or a food barrel or a silo or storage device. Monitoring can be used to check the quality of the medium contained in the tank. For example, a tank can contain cow's milk, the quality of which needs to be monitored during storage and/or transport. The container can also be a component of a beer or wine barrel or a wine or sparkling wine bottle for bottle fermentation. The container can be designed to monitor the fermentation process of the beverage.

A container can also be a component of a laboratory device, in particular a chemical laboratory device. For example, a container can represent a column for column chromatography.

According to one aspect, the wall protrusion, in particular the slit and/or the sample volume, comprises a channel or a channel-shaped volume, which is at least partly enclosed or surrounded by a channel guide and/or a guide plate or guide section. The channel is designed to guide a moving medium from a channel inlet to a channel outlet in one flow direction. The medium can flow through the sample volume, for example when the medium is agitated or mixed.

In other words, a wall protrusion comprises a flow channel or channel protruding into the container interior or bioreactor interior to collect medium from the container interior and to conduct the medium through the channel and substantially through the sample volume. In particular, a medium flows through the channel if the medium is mixed, agitated or moved by a stirring device in the container interior.

The advantage of a channel is that at least a part of a medium, which is moved through the container, in particular by means of a stirring device, can be "captured" by a channel opening and guided through the channel in a predetermined flow direction. In this manner, the medium in the sample volume can be exchanged efficiently, which is desirable, for example, if a process is running inside the container and a representative sample is to be examined in the sample volume.

Figure 4:
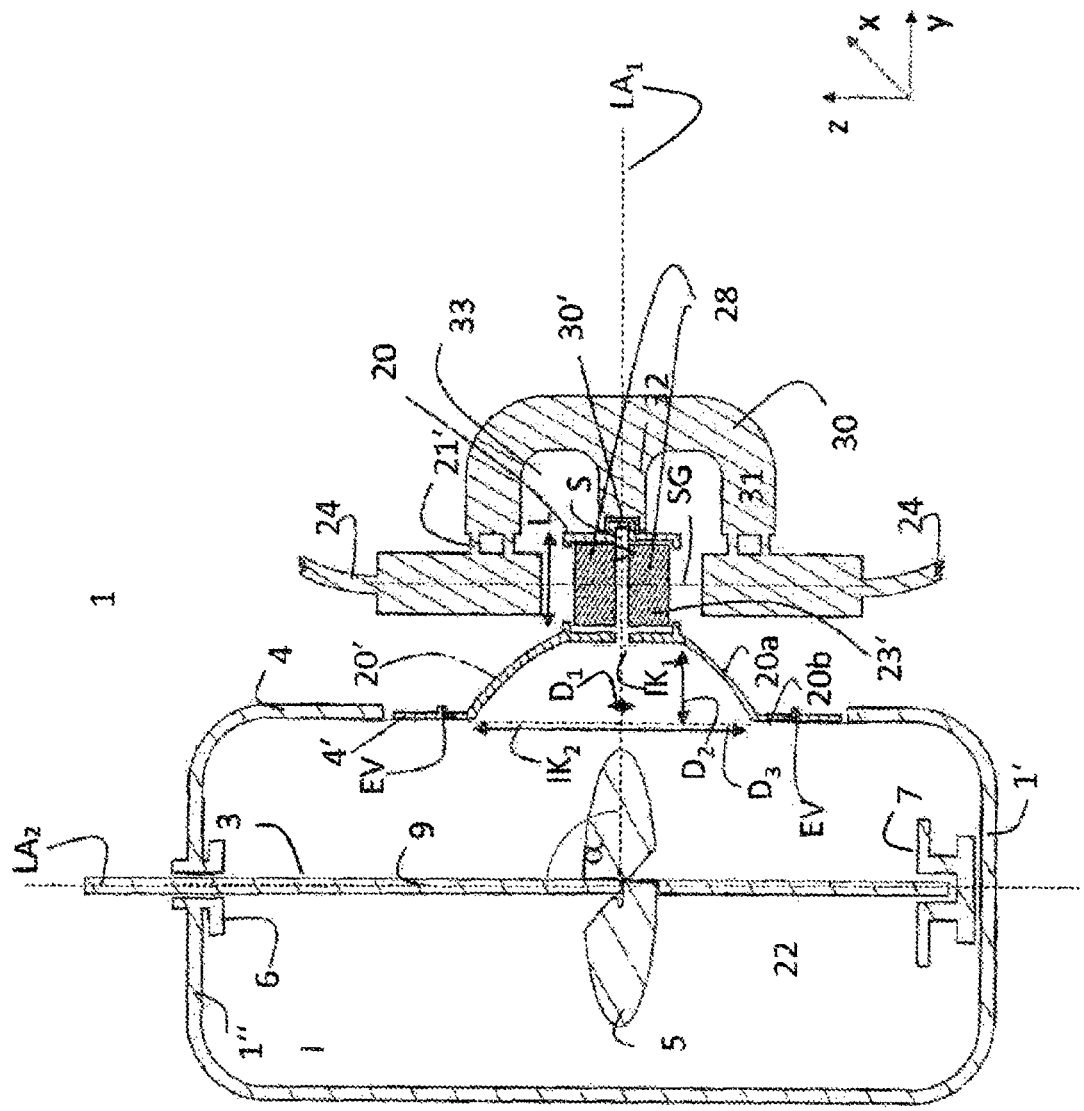
Figure 5:
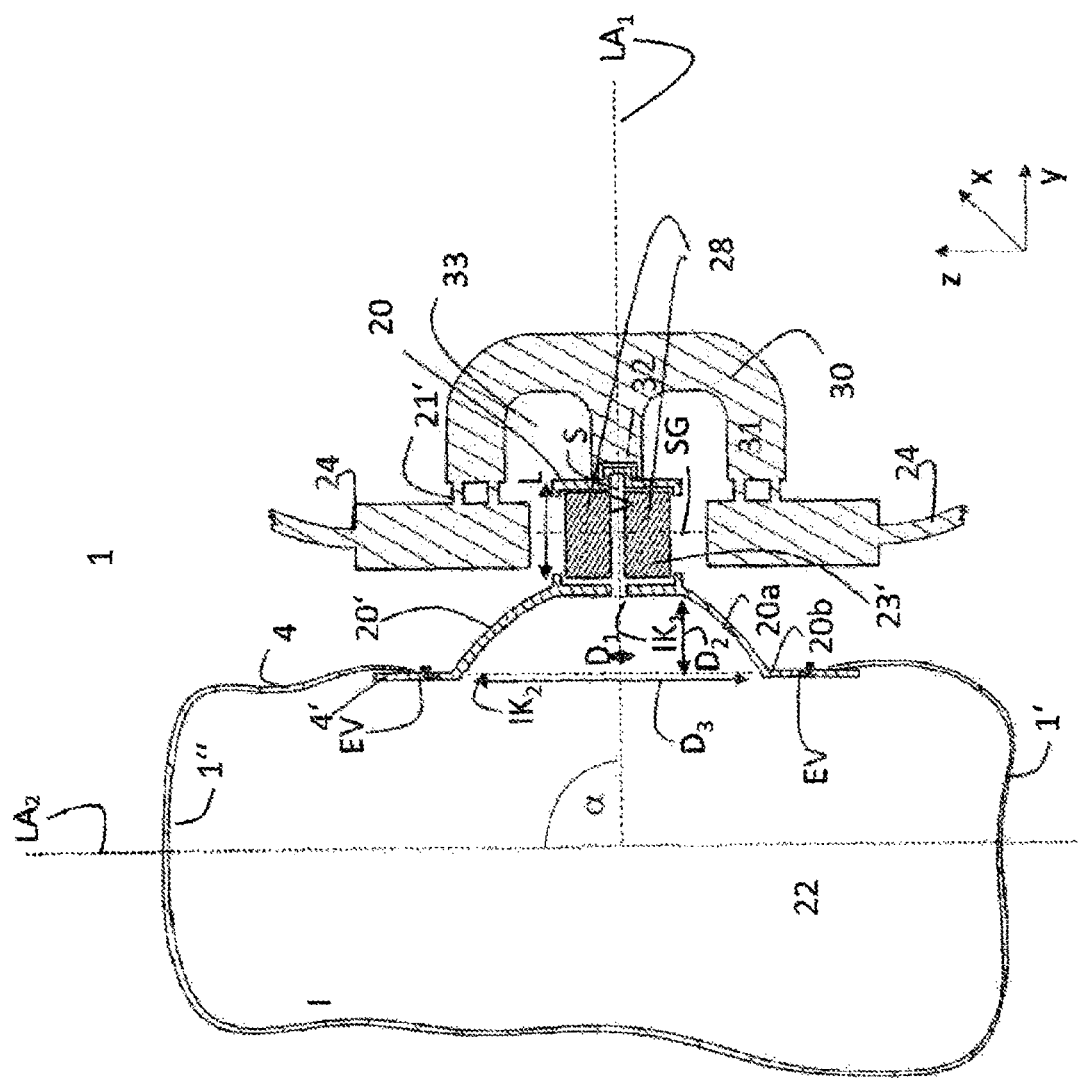
Figure 6:
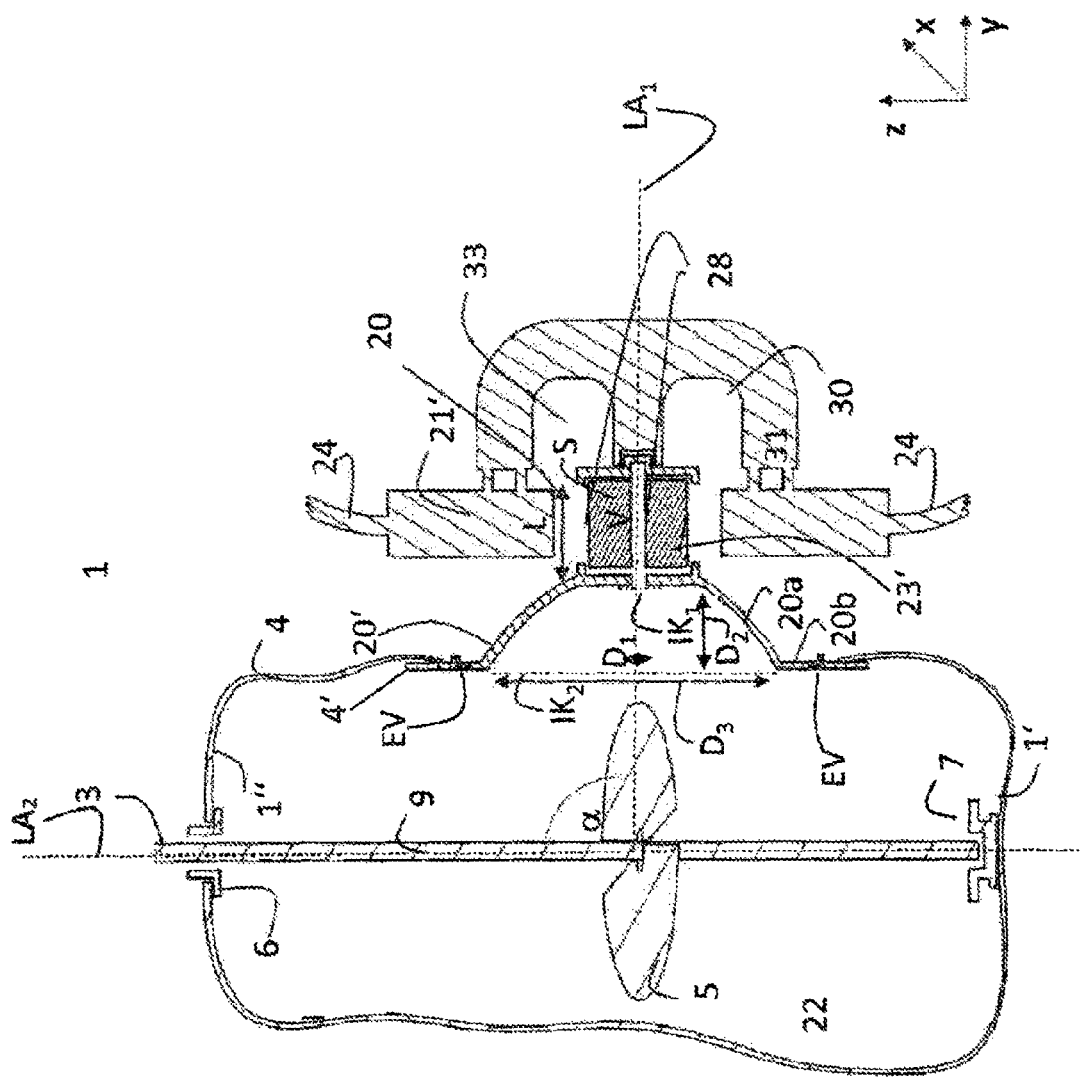
Figure 8:
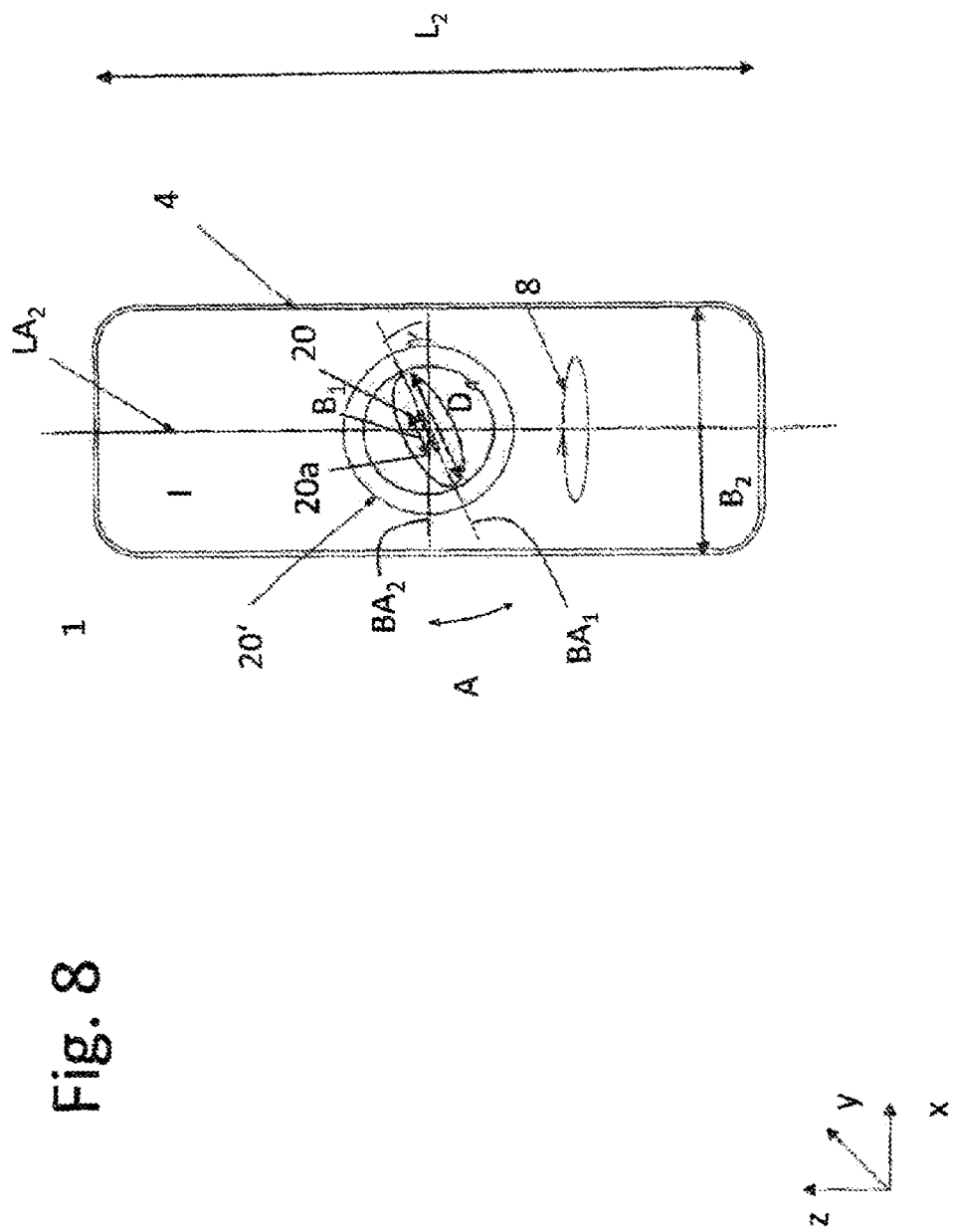
Figure 9:
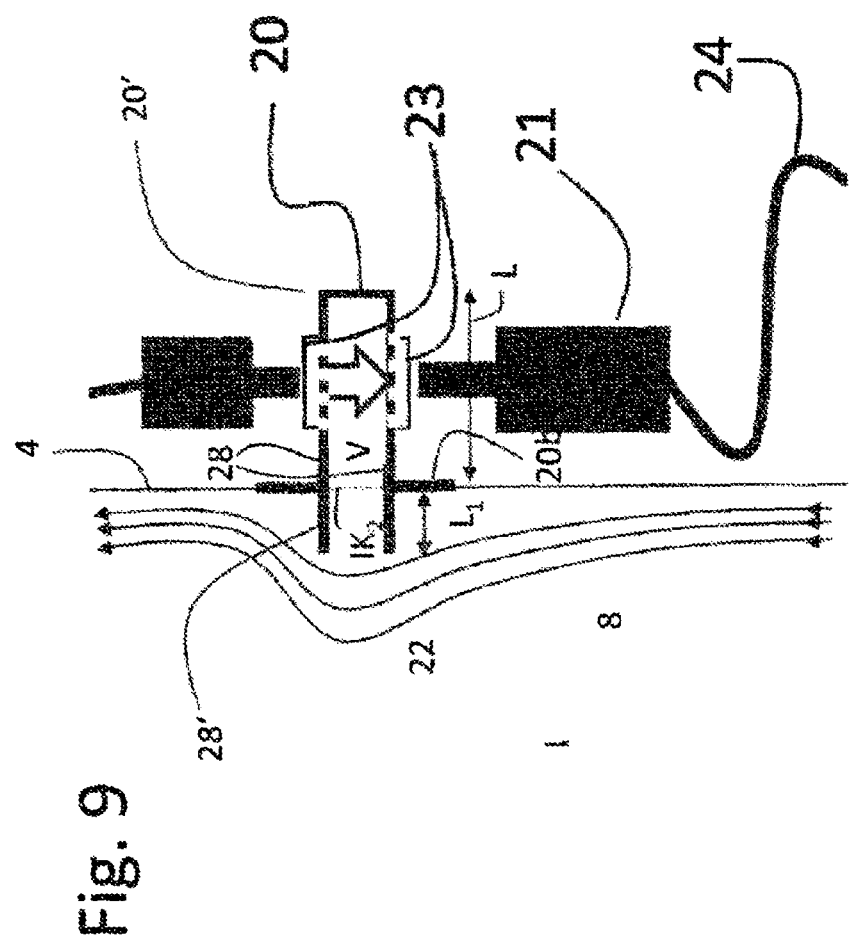

The invention is explained in more detail in the following on the basis of exemplary embodiments shown in the figures. Individual features shown in the figures can be combined with other exemplary embodiments to the extent that they are not mutually exclusive. Identical reference signs indicate identical or similar components of the embodiments. The following are shown:

FIG. 1 a schematic side view of a bioreactor with a wall protrusion and an optical measuring device according to one embodiment;

FIG. 2a a schematic side view of the cross-section of a bioreactor with a wall protrusion and an optical measuring device according to an additional embodiment;

FIG. 2b a schematic enlarged side detailed view of the cross-section of the wall protrusion on a container wall in accordance with FIG. 2a;

FIG. 3a a schematic detailed view of a wall protrusion with two sensor regions and a transmissive beam path arrangement;

FIG. 3b a schematic detailed view of a wall protrusion with a sensor region and a reflective beam path arrangement;

FIG. 3c a schematic detailed view of a wall protrusion with a sensor region, a reflective beam path arrangement, an access point and a pH sensor;

FIG. 4 a schematic cross-section of a bioreactor with a stirring element, a wall protrusion, a wall bulge and an optical measuring device according to one embodiment;

FIG. 5 a schematic cross-section of a disposable bag or disposable bioreactor with a wall protrusion, a wall bulge and an optical measuring device according to one embodiment;

FIG. 6 a schematic cross-section of a disposable bag or disposable bioreactor with a stirring element, a wall protrusion, a wall bulge and an optical measuring device according to one embodiment;

FIG. 7a a detailed section of a side view of a wall protrusion element with a wall protrusion, a wall bulge and a sensor attaching device according to one embodiment;

FIG. 7b a schematic cross-section of a side view of a wall protrusion element with a wall protrusion, a wall bulge and a sensor attaching device according to one embodiment as well as a connection point between a container wall and a wall protrusion element according to one embodiment;

FIG. 8 a schematic frontal view of a bioreactor with a wall protrusion inclined with respect to the width axis of the container and a wall bulge according to one embodiment;

FIG. 9 a schematic detailed view of a wall protrusion with two sensor regions and a transmissive beam path arrangement as well as an extension of the protrusion walls of the wall protrusion according to one embodiment;

FIG. 10a a perspective view of a wall protrusion element with a guide plate according to one embodiment;

FIG. 10b a view from the inner side of the wall protrusion element of FIG. 10a with a guide plate according to one embodiment;

FIG. 10c a view of a section along the line A-A through the wall protrusion element with a guide plate of FIG. 10b according to one embodiment from above;

FIG. 11a a perspective view of a wall protrusion element with a channel guide according to one embodiment;

FIG. 11b a view from the inner side of the wall protrusion element of FIG. 11a with a channel guide according to one embodiment;

FIG. 11c a view of a section along the line A-A through the wall protrusion element with a channel guide of FIG. 11b according to one embodiment from above.

FIG. 1 is a side view of a container 1, which is a component of a bioreactor, according to one embodiment (as an exemplary embodiment of a container with at least one wall protrusion for attaching or receiving or mounting or fixing at least one sensor) with a mixing system or a stirring element 3. Preferably, at least the container 1 is designed for disposable use and the container is in particular a disposable bag. Alternatively, the container 1 can also be a reusable container, for example a steel tank. Furthermore, the container does not necessarily have to be a component of a bioreactor.

In addition to the container 1 and the stirring element 3, which can be understood as a mixing system or a stirring device, the bioreactor also comprises a three-phase motor 10 as a three-phase machine for the stirring element 3. The stirring element 3 is designed to mix and agitate a medium 8 in the container 1. The medium 8 can comprise a fluid, in particular a liquid and/or a solid and/or a gas, and can in particular be in the form of a fluid mixture and/or a solid mixture or mixture of solids, or also in the form of a mixture of at least one fluid and at least one solid.

The container 1 according to the embodiment shown is penetrated by a stirring shaft 9 of the stirring element 3, which is arranged on the container inner side I of the container 1 and completely penetrates the container 1 from one end to an opposite end, i.e., from a container top 1" to a container bottom 1', along the longitudinal axis $LA_2$ of the container 1.

The longitudinal axis $LA_2$ of the container 1 extends substantially along or in parallel to the height of the container from the container bottom 1' to the container top 1" and in parallel to the z axis of the coordinate system shown.

The bioreactor also has a drive device 2, which is arranged outside the container 1. The stirring element 3 or the stirring shaft 9 is coupled to the drive device 2. The stirring shaft 9 of the stirring element 3 is substantially rod-shaped. The stirring shaft 9 is substantially completely arranged inside (on the container inner side I) of the container 1. In the embodiment, the stirring shaft 9 is mounted on a bearing 6 on the drive side and on a counter bearing 7. The bearing 6 on the drive side is arranged immediately adjacent to the drive device 2, while the counter bearing 7 is arranged on the side of the container 1 opposite the drive device 2. Several stirring extensions 5 are formed on the stirring shaft 9 and are designed to move around an axis of rotation of the stirring element 3 when the stirring shaft 9 rotates, and to mix the medium 8 if the container 1 is filled with a medium 8. The container interior 22 on the inner side I of the container 1 can be completely or partly filled with a medium 8. In particular, the container 1 can be at least partly filled with a medium 8 at the time of a measurement.

The container 1 of a bioreactor 1 and/or the bioreactor can alternatively also be designed without a stirring element 3, a stirring shaft 9, a drive device 2, a bearing 6 on the drive side and a counter bearing 7, in particular without any element that can serve to mix the medium 8.

A wall protrusion 20, which extends over a length L, is located on the container wall 4 of the container 1. The length L of the wall protrusion 20 extends substantially along a longitudinal axis LA₁ of the wall protrusion 20, which, in the embodiment, has an angle α of substantially 90° to the longitudinal axis LA₂ of the container 1. The longitudinal axis LA₁ also extends substantially in parallel to the y axis of the coordinate system shown.

Preferably, the container 1 with the wall protrusion 20 is formed in two combined or assembled or glued or welded pieces of the container 1 and the wall protrusion element 20'. In this case, the two pieces comprising respectively the container 1 and the wall protrusion 20 or the wall protrusion element 20' can be combined, assembled, glued and/or welded together with the wall protrusion 20, provided that they have not already been combined to form one object. The wall protrusion element 20' comprises the wall protrusion 20 as well as a section 20b for attaching the wall protrusion element 20' to the container 1. The wall protrusion element 20' is arranged or attached or attachable to the container 1 or to the container wall 4 of the container 1 by means of section 20b for attaching the wall protrusion element 20'. The container wall 4 has an opening or a hole that is sealed and covered by attaching the wall protrusion element 20' or the wall protrusion 20. The opening in the container wall 4 allows the entire container interior 22, i.e., the sample volume V, to be connected and in contact with the rest of the container interior 22. Thus, a material exchange or an exchange of a medium 8 can take place in both partial spaces of the container interior 22.

The wall protrusion 20 can, for example, be of the same strength or layer thickness as the container wall 4 and can at least partly surround at least a part of the container interior 22. The wall protrusion 20 can also be formed in a different strength or wall thickness or layer thickness than the rest of the container wall 4. For example, the wall protrusion 20 can substantially have, at least in part, a thinner wall thickness or strength than the rest of the container wall 4, for example one-half or one-third less. Alternatively, the wall protrusion 20 can also substantially have a wall thickness or strength that is at least partly thicker than the rest of the container wall 4, for example one-half or one-third thicker. The wall protrusion element 20' comprising the wall protrusion 20 can also substantially have a wall that is at least partly or in sections reinforced and/or thicker than the container wall 4.

The wall protrusion 20 at least partly surrounds a sample volume. In the embodiment shown, the sample volume V is designed as a slit S or a slit-shaped volume. The wall protrusion 20 protrudes away from the container wall 4 in the direction of the outer side A. In this case, the wall protrusion 20 and its two protrusion walls 28 protrude substantially at a right angle to the container wall 4 and also at a right angle to the walls of the section 20b for attaching the wall protrusion element 20' to the container 1. In this case, the two protrusion walls 28 extend in parallel to the longitudinal axis LA₁ of the wall protrusion 20, wherein the container wall 4 extends in a direction parallel to the longitudinal axis LA₂ of the container 1.

A curved arrow on the wall protrusion 20 on the container inner side I indicates that a medium 8 can flow or run at least partly through the sample volume V, in particular the slit S. In other words, the specific design ensures that a medium 8 (in particular liquid and/or gas) located in the container 1 can flow into and/or out of the sample volume V.

The container interior 22 contains the sample volume V and is connected to it, in particular via an opening. The container interior 22 without the sample volume V is referred to as the "rest of the container interior 22." If the container interior 22 is sufficiently filled with the medium 8, the medium 8 is also located in the sample volume V, in particular in the slit-shaped sample volume V, in such a manner that the wall protrusion 20 also at least partly surrounds or at least partly encloses a part of the medium 8. In other words, the medium 8 can fill a sample volume V, in particular a slit S, or flow into a slit S. In particular in the case in which the medium 8 is substantially mixed, for example by means of the stirring element 3, in the container interior 22, a flow or stream of the medium 8 can also flow or run through the sample volume V. Thus, a medium 8 in the sample volume V, in particular in the slit S, can be exchanged substantially temporarily or constantly or continuously with a medium 8 from the rest of the container interior 22. If a process, in particular a chemical, biological and/or biochemical process, takes place within the container 1, it can therefore be ensured that a representative part of the medium 8 from the container interior 22 is also present within the sample volume V and that a spatially inhomogeneous process can be substantially avoided.

The wall protrusion 20 shown in FIG. 1 comprises two sensor regions 23, wherein each sensor region 23 is attached to one of the two parallel long protrusion walls 28 so that the sensor regions 23 also face each other in a substantially parallel manner. From at least one of the two sides of the protrusion walls 28, a measuring access point (in particular optical access point) can thus be provided by means of the sensor regions 23 to the medium 8 in the container interior 22, in particular in the sample volume V and preferably a slit-shaped sample volume V. The sensor region 23 or measurement access point (for example, an optical access point) is or comprises an optical element, preferably a window 23'. Alternatively, a window 23' could generally be replaced by another optical element, such as a lens, prism, filter, iris and/or pinhole. The window 23' is substantially given by its at least partial transparency to light or electromagnetic waves with a certain or determinable wavelength spectrum and is not substantially limited to transparency to visible light. It is also possible that a sensor region 23 is not transparent to visible light but is transparent substantially to light of another non-visible wavelength (for example, in the infrared range). This can be advantageous, for example, if the process or the medium 8 in the container 1 is sensitive to visible light but nevertheless variables, in particular physical and/or chemical and/or biological variables of the medium 8, are to be measured by means of optical measurements. In this case, for example, a sensor region 23 can be at least partly made of silicon, which is transparent to infrared radiation but substantially non-transparent to visible radiation or has a significantly reduced transparency or permeability (for example, less than approximately 10%). However, it is also possible that the sensor region 23, in particular the window 23', is at least partly transparent to light of a substantially visible spectrum and at least partly transparent to light of a substantially invisible spectrum. The term "window 23'" accordingly comprises a flat element that is substantially transparent and has a correspondingly translucent surface. Two windows 23', in particular opposite windows 23', can be designed and/or manufactured as two separate elements. Alternatively, two windows 23' can also be made in one piece, i.e., in one continuous element. In other words, two or more windows 23' do not have to be manufactured separately from each other but can consist of one piece. In particular, the wall protrusion 20 can be substantially made of a transparent material and thus naturally have the characteristics of the windows.

Preferably, as mentioned above, the term "sensor region 23" refers to a window 23' if it is a sensor region 23 for sensing optical variables by means of an optical sensor device 21. Alternatively or additionally, a sensor region 23 can also comprise or represent an access point and/or an opening.

Relative to the wall protrusion 20 shown in FIG. 1, a sensor or sensor device 21 is attached or can be attached from the outer side A or from the outside. In the embodiment, the sensor device 21 comprises a light conductor 24 or a fiber optic cable or an optical fiber, a light conductor incoupling section 24a as well as a sensor unit, which is represented in FIG. 1 by a spectrometer 25. In this respect, it can be assumed that a light conductor 24 or fiber optic cable substantially corresponds to an optical fiber. An optical beam path or a light path or a path followed by a light through the sensor regions 23 and the sample volume filled with at least a part of the medium 8 is shown in FIG. 1 as a transmissive beam path arrangement T. On a side opposite the sensor device 21, a light conductor outcoupling section 24b with an additional light conductor 24, also called a fiber optic cable, is shown in accordance with the embodiment as shown in the drawing. This light conductor outcoupling section 24b can, for example, serve as a light source through which light of a predetermined or predeterminable spectrum is decoupled and sent into or through the sensor region 23 and the sample volume. For example, the light can interact at least partly with the medium 8 in the sample volume V in such a manner that it is at least partly absorbed, in particular by excitation of the molecules of the medium 8.

Preferably, a light or a (preferably collinear) light beam runs substantially along or at least partly in parallel to a beam path axis SG through the sample volume V, as indicated in FIG. 1. A beam path axis SG can be defined by the course of a light beam, wherein the beam path axis SG runs substantially in the middle or centrally within the cross-sectional area of the light beam substantially along the propagation direction of the light beam. An example of such a beam path axis SG is shown in FIG. 1 to indicate the possible course or propagation axis or propagation directions of a light beam. For this purpose, the light conductor incoupling and outcoupling sections 24a, 24b are arranged on the wall protrusion 20 in such a manner that a light beam that emerges from the light conductor outcoupling section 24b is propagated or runs substantially along or at least in parallel to the beam path axis SG through the sample volume V or the slit S and the sensor regions 23 or the window 23' in order to then be at least partly sensed or captured or picked up by the light conductor incoupling section 24a or to be coupled into the light conductor incoupling section 24a. Essentially, the beam path axis SG and thus the direction of propagation of a light beam runs substantially in parallel on the outer side A to an adjacent container wall 4 of the container 1.

Instead of a bioreactor as shown in FIG. 1, it could also be a food tank, a pellet tank, a storage tank, a mixing tank or other container.

FIG. 2a shows a side view of an embodiment of a bioreactor with its container 1, wherein the bioreactor is a disposable bioreactor and the container 1 is a "single use" or disposable bag or disposable container. The bioreactor thus comprises a container 1 and a mixing system for at least partial disposable use. The bioreactor comprises a stirring element 3, a stirring shaft 9 and a stirring extension 5. In this case, the stirring device or stirring element 3 can, for example, also be at least partly suitable for reusable use, whereas the container 1 and substantially the outer skin or the container wall 4 is suitable and/or intended for disposable use. It is also possible that the stirring device or stirring element 3 is also completely designed for one-time use or usage. The disposable container 1 can substantially be a plastic bag that can, for example, be stored and/or suspended inside another rigid container, such as a tank and/or a frame.

In other words, at least the outer skin or container wall 4 of the bioreactor, which at least partly shields or delimits or separates the container interior 22 or the container inner side I from the outer side A, can at least partly comprise a plastic, in particular a soft plastic or a particularly flexible plastic. In particular conceivable are soft PVC, polyolefin, polyethylene, polycarbonate, cyclo olefin copolymer, co-polyester and/or polystyrene. Furthermore, the container 1 can be made of a single-layer or multi-layer plastic material, which is particularly resistant or stable against beta or gamma radiation. In general, the container interior 22 of a container 1 can constitute a closed system, which can be preferred in particular for anaerobic processes and/or where light irradiation is excluded. Furthermore, to the exclusion of light irradiation, the container wall 4 can be partly and substantially non-transparent (for example, with less than approximately 10% transparency) to light in all spectral ranges or at least to light of a certain spectral range and can filter out or absorb at least a part of the wavelength spectrum of electromagnetic radiation, in particular the visible spectrum.

A disposable container 1 can be quite sensitive or delicate to mechanical influences under certain circumstances. For example, an attempt to take a sample and/or monitor a process by means of a measurement can result in damage to the disposable container 1, for example by accidental crushing and/or puncturing. A wall protrusion 20, as shown schematically in FIG. 2a, for attaching a sensor or detector, a sensor device 21 or several sensor devices 21 can be particularly advantageous for handling a disposable container 1 and its medium 8 contained in the container interior 22, if variables, in particular physical and/or chemical and/or biological variables of the medium 8, are to be sensed. In particular, the substantially non-invasive process control, which is made possible thereby, results in the medium 8 in the container interior 22 substantially not being contaminated, for example with substances from outside that are harmful to the process flow, in particular microbiological substances and/or oxygen.

A disposable container or disposable bag 1, as schematically illustrated in FIG. 2a, can be formed in such a manner that the outer skin or container wall 4 at least partly curves outward or toward the outer side A, if the container interior 22 is at least partly filled with a medium 8.

The container wall 4 can at least behave flexibly and/or in an extensible manner and/or like a sack when the contained medium 8 is filled and/or emptied. By sensing the variables of the medium 8, this characteristic makes handling particularly difficult when monitoring a process running in the container interior 22. For this reason, it is particularly preferred that a rigid or dimensionally stable wall protrusion 20 is attached to or arranged on or fastened to the container wall 4. The wall protrusion 20 can, for example, be a part of a wall protrusion element 20', and/or can be attached to or arranged on a wall protrusion element 20'. The wall protrusion element 20' is preferably rigid or dimensionally stable. The wall protrusion element 20', which comprises the wall protrusion 20, can therefore be attached to or arranged on, in particular glued to and/or welded to, the container wall 4 of a disposable container. For this purpose, the wall protrusion element 20' can comprise a section that at least partly mimics or specifies a shape of the container wall 4 so that a transition between the container wall 4 and the wall protrusion element 20' which is continuous in terms of shape is produced after attaching. It is preferable that the wall protrusion element 20' is formed in one piece with the wall protrusion 20, for example by welding, casting and/or 3D printing techniques. Alternatively, the disposable container 1 can also as a whole be constructed in one piece with the wall protrusion 20.

The wall protrusion element 20' and in particular the wall protrusion 20' is preferably at least partly molded from a so-called hard plastic or from a stiffer or more dimensionally stable plastic, in particular from a (meltable) thermoplastic or from a (non-meltable) thermoset, for example a synthetic resin. In particular, the plastic can be sterilized, for example by means of beta or gamma radiation. In general, the material used to manufacture a container 1 or to make a reusable or disposable bioreactor can be sterilized by means of thermal sterilization, by means of steam sterilization, by means of hot air sterilization, by means of chemical and/or physical sterilization (for example, beta or gamma irradiation).

The dimensionally stable formation of the wall protrusion 20 ensures that a sample volume V, which can be filled with the medium 8 from the container interior 22, always maintains a substantially constant value. This facilitates the comparison of variables or parameters that are measured continuously or sporadically over a longer period of time since no corrections due to a (possibly unknown) change in layer thickness have to be considered. In this manner, a background measurement or calibration that can be regarded as valid over the entire period of data acquisition can be carried out at the beginning of data recording or the sensing of variables in particular.

As shown schematically in FIG. 2a in accordance with the embodiment shown, the disposable container or disposable bag 1 has a shape which is curved outward or toward the outer side A and is not strictly predefined, whereas the wall protrusion 20 has an at least partly well-defined contour or shape. It is easy to imagine how cumbersome it can be to handle such a container 1 without a wall protrusion 20 when sensing variables of the content or the medium 8. In particular, an exact reproducible alignment of optical elements can be cumbersome or even impossible for a disposable container 1 without a wall protrusion 20 but with an optical system mounted in a weld-in port since weight forces would act on such a weld-in port due to the medium 8 contained. Such a weld-in port could, for example, comprise a bulge which is directed toward the container inner side I and which comprises an opening or access point for a sensor or for taking samples. This would lead to a bulging of the weld-in port, which in turn could affect the beam path. For this reason, the wall protrusion 20 has many advantages over a weld-in port with optical elements. As already described for the container 1 in FIG. 1 and not further explained here, an identical sensor device 21 as in FIG. 1 is attached to the wall protrusion 20 on the outer side A, wherein process monitoring can be carried out by means of an optical method by means of a transmissive beam path arrangement T through two sensor regions 23. Thus, the proposed embodiment with an outward extending wall protrusion 20 is advantageous since it can be designed to be particularly stable, in particular dimensionally stable, with respect to weight forces of the medium 8 within a container 1. In this manner, it can substantially be prevented that a volume or sample volume V to be examined changes, in particular with regard to its variable and/or shape, or bulges and/or deforms due to forces. For this reason, the described embodiment can substantially ensure or make possible that a sample volume V can be repeatedly examined, in particular optically, under particularly constant conditions. This can, for example, require and be ensured by the embodiment in particular that an optical beam path or an optical path or a path taken by a light, for example a laser beam, in particular along the beam path axis SG through the sample volume V, is particularly stable or constant. Furthermore, the outward bulge ensures in particular that the (direct or indirect) coupling or attaching of the sensor device 21 is easily ensured. A corresponding measurement is ensured in a particularly simple manner, in particular by the one or more sensor regions 23 that are accessible from the outside or from the side and that are windows 23' in the embodiment.

The wall protrusion element 20' can be generally understood as a port or comprise a port, wherein a port is characterized in that it comprises elements that are suitable as means for attaching or mounting or fastening a sensor attaching device 30 relative to the wall protrusion 20. Preferably, a wall protrusion 20 has a bearing clearance in an attached state.

Thus, the optical path or the optical beam geometry is substantially defined only by the sensor attaching device 30 and by the geometry and composition of the wall protrusion 20 and is almost independent of forces acting on the port. This can be an advantage for convenient, simple and proper use if a manufacturer can make the adjustment prior to the sale of a sensor attaching device 30 and the user only needs to attach the sensor attaching device 30 to the wall protrusion element 20' or relative to the wall protrusion 20 in order to carry out or undertake a measurement.

In particular, the process of attaching the sensor attaching device 30 to the wall protrusion element 20' can prove to be particularly uncomplicated and simple in this case. The adjustment of the optics or the beam geometry on the sensor attaching device 30 can be done prior to attaching. In particular, a light conductor incoupling or outcoupling section 24a, 24b can be simply clipped or clamped to the port or wall protrusion element 20', preferably by means of the sensor attaching device 30. Moreover, the attachment of the light conductor 24 or the light conductor incoupling or outcoupling sections 24a, 24b to the sensor attaching device 30 can be carried out prior to or after the attaching of the sensor attaching device 30 to the container 1.

FIG. 2a also indicates a beam path axis SG, along which a light beam substantially propagates. Preferably, this beam path axis SG runs substantially in parallel on or to the outer side A to the adjacent container wall 4, although it is also possible that the container wall 4, as indicated in FIG. 2a, has an outward bulge, which results in the beam path axis SG not being parallel to the container wall 4, at least in sections. Nevertheless, it is preferred that the beam path axis SG and thus the direction of propagation of a light beam is substantially perpendicular to and/or through the slit S, the protrusion walls 28 and the sensor regions 23 or the windows 23'. As already mentioned, one advantage of this embodiment is therefore in particular that a wall protrusion 20 is particularly dimensionally stable, whereas the container wall 4 can deform and/or bulge. This has the effect that a beam path axis SG can be set to be stable and/or reversible and that particularly stable measuring conditions can be given.

FIG. 2b is an enlarged detailed view of the wall protrusion 20. The wall protrusion element 20' comprises the wall protrusion 20 and a section 20b for attaching the wall protrusion element 20' to the container 1. The section 20b can preferably adapt to the shape of the container wall 4 or has a substantially rigid shape that is already adapted to the container wall 4. In the embodiment of FIGS. 2a and 2b, the wall protrusion 20 comprises two sensor regions 23, which are windows 23'.

The wall protrusion 20 with the sample volume V is substantially outside the radius of curvature of the disposable bag or the bulged disposable container 1. In other words, the sample volume V or the slit S and thus the wall protrusion 20 protrudes outward from the container wall 4. The wall protrusion 20 at least partly surrounds the sample volume V, which is designed in the form of a slit S. The sample volume V is the volume or space of the container interior 22, which is largely surrounded by the wall protrusion 20. The sample volume V is delimited from the other part of the container interior 22, which is substantially surrounded by the container wall 4, by an imaginary contour line $IK_1$ (dotted line in FIG. 2b). The imaginary contour line $IK_1$ is substantially the extension of the container wall contour or the connecting line between the lines of the container wall contour, wherein the container wall contour is the contour of the container wall without a wall protrusion 20. Thus, the container wall contour does not comprise the contour of the wall protrusion 20. As mentioned above, this defines the sample volume V, which is located outside the imaginary contour line $IK_1$.

If a wall protrusion element 20' comprises a wall bulge 20a, the imaginary contour line $IK_1$ is however defined by the contour of the wall bulge 20a. The imaginary contour line $IK_1$ is then substantially the extension of the contour of the wall bulge 20a or the connecting line between the contour lines of the wall bulge 20a, wherein the contour of the wall bulge 20a does not comprise the contour of the wall protrusion 20.

A wall protrusion element 20' always comprises a wall protrusion 20. The wall protrusion element 20' can also comprise a wall bulge 20a. In addition, the wall protrusion element 20' can comprise a section 20b for attaching the wall protrusion element 20' to the container 1. In particular, a wall protrusion element 20' and preferably a section 20b for attaching can also comprise a part of an element connection EV. For example, a part of the element connection EV can be a thread that can be screwed into a compatible thread on the container wall 4.

In other words, the sample volume V is that volume of the container interior 22 that extends from the imaginary contour line $IK_1$ (dotted line in FIG. 2b) of the contour or imaginary contour line of the container wall 4 or the contour or imaginary contour line of the wall bulge 20a over a length L along the longitudinal axis $LA_1$ with the sample layer thickness $D_1$ of the wall protrusion 20.

An alternative embodiment to the embodiment shown in FIGS. 2a and 2b, which is not explicitly shown here, comprises, instead of two opposite windows 23', one window 23' and, opposite thereto, a combination of a window 23' and a mirror or reflector. For example, the upper wall of the wall protrusion 20, in particular with respect to the z direction shown, or the upper protrusion wall 28 can comprise a window 23', and the lower protrusion wall 28 can comprise a window 23' and a mirror and/or reflector. For example, the surface of a window 23' could be at least partly overlapped by the surface of a reflector, wherein the reflective side of the reflector points in the direction of the opposite window 23'. In this case, measurements under transmission and reflection can be performed simultaneously. This means that both a transmissive beam path arrangement T and a reflective beam path arrangement R can be used at the same time. In particular, this allows several types of spectroscopy with different optical geometries to be used.

Preferably, the longitudinal axis $LA_1$ of a wall protrusion 20, as indicated in FIG. 2b, has a substantially right angle to the beam path axis SG. This applies to a transmissive beam path arrangement T in the same way as to a reflective beam path arrangement R. Preferably, the longitudinal axis $LA_1$ of the wall protrusion 20, as indicated in FIG. 2b, also has a substantially right angle to the imaginary contour line $IK_1$. Thus, the imaginary contour line $IK_1$ is substantially parallel to the beam path axis SG, at least in places.

FIGS. 3a to 3c show schematic and detailed side views of three different embodiments of the wall protrusions 20, which are attached to a container wall 4. Individual features of different embodiments can be combined with each other as long as they are not mutually exclusive. Such wall protrusions 20 can be attached to any container 1, for example to the container wall 4 of a reusable container 1 of a reusable bioreactor or to the container wall 4 of a disposable container 1 of a disposable bioreactor or to the container wall 4 of a barrel, a canister, a tank, a food tank, a transport container and/or to a container other than those already mentioned.

The wall protrusion 20 of all embodiments, as is already the case for other embodiments, at least partly surrounds a sample volume V, which is defined, among other things, by a sample layer thickness $D_1$ and a protrusion length L and is in contact or fluid exchange with the rest of the container interior 22 or is a part thereof. In this manner, a medium 8 can flow into the sample volume V during filling into the slit S and, in particular, can be exchanged with the medium 8 from other positions of the container interior 22. However, there can also be a shutter device (not shown here) that can be operated from the outside and that isolates and/or separates the sample volume from the rest of the container interior 22 by operation. This can be particularly advantageous if a measurement or sensing of variables is not to be disrupted by processes within the container 1, for example by a stirring process. This also prevents a process on the container inner side I beyond the sample volume V from being disrupted by the incidence of light through the windows 23'.

The wall protrusion 20 shown in FIG. 3a comprises two sensor regions 23, which are also designed as a window 23' and which are correspondingly at least partly transparent or translucent to electromagnetic radiation. In the examples in FIGS. 3b and 3c, the wall protrusion 20 respectively comprises only a single window 23'. The wall protrusion 20 shown in FIG. 3a comprises two protrusion walls 28, which are substantially parallel to each other and have a length that substantially corresponds to the protrusion length L if the layer thickness of the wall of the wall protrusion 20 is disregarded.

The two protrusion walls 28 and/or sensor regions 23 and/or windows 23' can alternatively also be aligned to not be parallel to each other. The advantage of a substantially parallel alignment, in particular of the windows 23', is the avoidance of scattered light or the reduction of scattered light that would occur if light were not to pass through perpendicularly, i.e., if the beam path axis SG would enclose a (substantially) smaller angle than 90° with the surface of at least one window 23b.

FIG. 3a shows, in a schematic detailed side view, a particular embodiment of a wall protrusion 20 to which an optical sensor device 21, in particular a light conductor incoupling section 24a and a light conductor outcoupling section 24b, for the application of an optical method, are attached from the outer side A by means of a sensor attaching device 30.

The sensor attaching device 30 preferably has a dimensionally stable or rigid frame or framework or attaching device body, which in particular is formed at least partly from a metal and/or a dimensionally stable plastic. The sensor attaching device 30 can preferably be reversibly attached to or removed from the wall protrusion 20 in such a manner that the same sensor attaching device 30 can be attached several times or reusably to a wall protrusion 20 and/or to wall protrusions 20 and/or container walls 4 of different containers 1.

Alternatively, the sensor attaching device 30 can be permanently attached to or relative to a section of the wall protrusion 20 and/or to or relative to the container wall 4. In particular, the sensor attaching device 30 can in this case preferably be fixed or firmly connected to the container wall 4 by means of a composite material and/or by means of a screw connection and/or by means of a weld seam.

The sensor attaching device 30 preferably comprises the optical elements of the sensor device 21, in particular comprising optical lenses and/or prisms and/or mirrors and/or particularly preferably light conductors or optical fibers and/or other beam guiding elements. If the sensor attaching device 30 does not comprise the mentioned optical elements, it can at least be designed to receive or mount or fix such optical elements. The sensor attaching device 30 and the optical elements, if comprised or mounted, substantially define the beam geometry of the optical elements of the sensor device 21. In particular, the sensor attaching device 30, along with the optical elements, defines the beam path axis SA or the geometry of the light beam through the sample volume.

The sensor attaching device 30 can, in particular, mount a sensor or a sensor device 21, in particular an optical measuring device, relative to a wall protrusion 20 in such a manner that, as shown in FIG. 3a, one or more variables can be sensed by means of a transmissive beam path arrangement T. For example, by means of a light conductor outcoupling section 24b or by means of another light source, a light or electromagnetic radiation, for example in a wavelength spectrum that includes infrared radiation, can be sent or radiated from outside through a sensor region 23 into the container interior 22, in particular at least into a section of the sample volume V.

The sensor attaching device 30 has a recess 33 that is at least partly filled with the wall protrusion 20 and the sample volume V when the sensor attaching device 30 is mounted on the container 1 and/or the wall protrusion 20. In other words, the sensor attaching device 30 can be mounted or attached relative to the wall protrusion 20 such that at least one section of the wall protrusion 20 and of the sample volume V, which can be at least partly filled with a medium 8, can be located within a recess 33 of the sensor attaching device 30. In other words, a wall protrusion 20 and a sample volume V can be at least partly surrounded by a wall of a recess 33 of a sensor attaching device 30.

If the sample volume V is at least partly filled with a medium 8, the electromagnetic radiation in the sample volume V can interact at least partly and substantially with the medium 8, in particular the molecules and/or atoms of the medium 8. In this manner, for example, electromagnetic radiation (or the irradiated light) can be at least partly absorbed and/or scattered by the medium 8. By means of a light conductor incoupling section 24a, the light that has entered through the medium 8 or has passed through the medium 8 can again be sensed. In the case of infrared spectroscopy, the concentration of a particular species of molecule, for example, can be determined in this way by absorbing light or electromagnetic radiation of certain wavelengths, in particular in the infrared spectrum. This can in turn give an indication of a stage of a process in which the medium 8 is located at the time of sensing the data or the variables or the parameters. Furthermore, it is possible that the at least one sensor region 23 has at least two electrical electrodes that can come into contact with the medium 8 in the container 1 so that a resistance measurement can be carried out between such electrodes in order to determine at least one property of the medium 8.

FIG. 3b shows, in a schematic detailed side view, a particular embodiment of a wall protrusion 20 with only one single sensor region 23, to which a (particularly optical) sensor device 21, particularly a light conductor incoupling section 24a, can be attached from the outer side A by means of a sensor attaching device 30. In particular, this is a transmissive beam path arrangement T. In addition to the light conductor incoupling section 24a, a light source (not shown here) can also be attached to the wall protrusion 20 or the light conductor incoupling section 24a can be used for coupling out and coupling in light.

In this manner, electromagnetic radiation can be irradiated through the sensor region 23 from outside into at least one section of the sample volume V. Alternatively or additionally, only one sensor of a sensor device 21 or a light conductor 24 of a sensor of a sensor device 21 can be attached relative to the sensor region 23, wherein the sensor of a sensor device 21 is designed, for example, to record a fluorescence of the medium 8. In this case, it is possible that it is substantially not necessary to irradiate light because a fluorescence can have been triggered, for example, by a chemical reaction in the container 1. The light of a fluorescent reaction can then pass at least partly through a window 23' from the container interior 22 to the outer side A, where it can be sensed by a sensor of a sensor device 21.

By means of reflection and/or scattering on at least one reflector 23b and/or scattering elements and/or scattering particles, light, provided it is not absorbed by the medium 8, can exit the container interior 22 or the sample volume V again through the sensor region 23 and can be sensed by the light conductor incoupling section 24a. For example, on the opposite side of the sensor region 23 on the opposite protrusion wall 28, a mirror or a reflector 23b or a scattering element, which can reflect light falling on it, can be attached on the container inner side I. By means of a light conductor 24, the sensed light can then be transmitted to a spectrometer 25, for example, where it can be broken down into its spectral components and analyzed by a computing unit and/or a user, for example. A scattering element can be a white surface or a diffractive element, such as a grating or other element that can scatter light.

FIG. 3b also indicates a beam path axis SG. It is possible that an incident light or light beam runs or propagates substantially along or in parallel to this beam path axis SG. It is also possible that in particular a (back) reflected light or light beam runs or propagates substantially along or in parallel to this beam path axis SG on its way to a sensor of a sensor device 21. Moreover, at least one part of a (back) scattered light or light beam can substantially run or propagate along or in parallel to this beam path axis SG on its way to a sensor of a sensor device 21.

Similar to FIG. 3b, FIG. 3c schematically represents on embodiment of the wall protrusion 20 with only one sensor region 23, one reflector 23b and one reflective beam path arrangement R. According to this schematic diagram, a light conductor incoupling section 24a is arranged relative to the wall protrusion 20 and in particular the sensor region 23. In this diagram, it is not clear how the attachment takes place since no sensor attaching device 30 is shown, but the attachment can still take place by means of the sensor attaching device 30. In addition to the sensor region 23, the wall protrusion 20 comprises an access point 26, which is designed so that a pH value of the medium 8 can be sensed from outside by means of a pH electrode. In particular, the pH electrode 27 can depend on or can be designed to ensure that there is contact between at least one section of the pH electrode 27 and the medium 8 in the container interior 22. This would be the case if at least one section of pH electrode 27 were to pass through the access point 26, in particular in the form of an opening, from the outer side A to the container inner side I, in particular into the sample volume V. In this manner, the pH electrode 27 can be attached temporarily or permanently to the wall protrusion 20 for the sensing of variables, in particular physical variables of the medium 8. The pH electrode 27 can comprise a line 29 or can be connected to a line 29, for example a power line and/or a data line.

Alternatively, a wall protrusion 20 can also comprise more than two sensor regions 23 and/or more than one access point 26. By means of a sensor attaching device 30, only one or a plurality of sensors 21 and/or sections of sensor devices 21 can be attached relative to the wall protrusion 20.

An additional embodiment, which is not explicitly shown here, substantially comprises a combination of the embodiments according to FIG. 3a and FIG. 3b or FIG. 3a and FIG. 3c. According to one embodiment, the wall protrusion 20 comprises a reflective element and/or a reflector and/or a mirror 23b and two sensor regions 23, each comprising a window 23'. The wall protrusion 20 is designed in this case so that a first variable or a first parameter can be sensed through a reflective beam path arrangement R by means of a first sensor device, which preferably comprises at least one first optical fiber 24, and a second variable or a second parameter can be sensed through a transmissive beam path arrangement T by means of a second sensor device, which preferably comprises a second optical fiber 24. The first variable can also be or comprise the second variable. This could be achieved by either making one window 23' slightly smaller than the other window 23' and instead having a reflector 23b take the place that the window 23' would take. In addition, the surface of a window can also be overlaid or spatially overlapped with the surface of a mirror and/or reflector from the outside or inside.

FIG. 4 is a schematic cross-section of a substantially dimensionally stable container 1, for example a bioreactor. It is a container with a stirrer and an attached or arranged fiber holder or sensor attaching device 30, wherein the fibers or light conductors 24 are aligned with respect to the wall protrusion 20 by means of the sensor attaching device 30 in such a manner that variables of the sample volume V can be recorded by the sensor device 21. In this embodiment as well, a container 1, in particular a disposable container, can be made, for example, from a material comprising PVC. However, the container 1 can alternatively be a reusable container, in particular of a fermenter, for example made of a material comprising steel and/or PVC. The bioreactor also comprises a stirring device or stirring element 3 with components that have already been described in more detail for other embodiments. A stirring shaft 9 extends from the container top 1" to the container bottom 1' substantially along the longitudinal axis $LA_2$ of the container 1.

The container 1 comprises a wall protrusion element 20', which has a wall bulge 20a with a height $D_2$ and a depth $D_3$, and a wall protrusion 20, which extends outward over a length L. The height $D_2$ of the wall bulge 20a extends substantially along an imaginary contour line $IK_2$ as an extension of the container wall 4 and as a boundary to the wall bulge 20a. However, the depth $D_3$ of the wall bulge 20a substantially extends from the imaginary contour line $IK_2$ as an extension of the container wall 4 to the imaginary contour line $IK_1$ for defining the sample volume V of the wall protrusion 20.

The wall protrusion 20 further comprises two windows 23, which are arranged in parallel to each other substantially at the distance of the slit-like sample layer thickness $D_1$.

A sensor attaching device 30 is mounted on or attached to the wall protrusion 20 by means of an attaching device bar 32 and a receiving element 30' for a sensor attaching device 30. The attaching device bar 32 comprises a guide channel through which a rail corresponding to the receiving element 30' of the wall protrusion 20 can be guided. As mentioned above, however, the type of connection or mounting can also comprise a clamp connection, a press connection, a pressure connection, a clip connection and/or a screw connection.

In the embodiment, the longitudinal axis $LA_1$ of the wall protrusion 20 forms a substantially right angle α with the longitudinal axis $LA_2$ of the container 1. However, the angle α can alternatively be an angle that substantially deviates from 90°. The imaginary contour line $IK_1$ for defining the sample volume V runs substantially in parallel to the imaginary contour line $IK_2$ as an extension of the container wall 4 and as a boundary to the wall bulge 20. Alternatively, the two imaginary contour lines $IK_1$, $IK_2$ can also run not in parallel to each other. This would be the case, for example, if the angle α does not amount to 90°.

FIG. 4 further indicates that the wall protrusion element 20' is connected or attached to each other via an element connection EV or a connection between the section 20b for attaching the wall protrusion element 20' to the container 1 and the container wall 4.

The wall protrusion element 20' and in particular the section 20b for attaching the wall protrusion element 20' to the container 1 can comprise a part of an element connection EV, whereas another compatible part of the element connection EV can be located on the container wall 4. This element connection EV, for example, can comprise two threads that can be screwed into each other.

Via the element connection EV, the wall protrusion element 20' can be attached or will be attached directly or indirectly to the container wall 4. The diagram of the embodiment of FIG. 4 indicates a wall section 4', which in turn is also attached to the container wall 4 and on which the element connection EV is positioned, which corresponds to indirect attachment or connection. The wall section 4' for connection or attachment between the wall protrusion element 20' and the container wall 4 can substantially be a reinforced section comprising a plastic and/or a metal. For example, the wall section 4' for the connection or attachment between the wall protrusion element 20' and the container wall 4 can be tightly glued and/or clamped and/or welded to the container wall. In this case, the wall protrusion element 20' and the wall section 4' can be understood as a two-part port. For example, an outer ring, which is welded to the container wall 4 (also to be understood as a bag wall), can be continuously and/or temporarily combined with or connected to or attached to an inner core, which corresponds to the wall protrusion element 20'. The connection of the wall protrusion element 20' with the ring or wall section 4' for the connection can comprise a bayonet lock, screws, clips, clamps, press or pressure connections and/or adhesive connections. In particular, the wall protrusion element 20' can be mounted on and removed from the container wall 4.

Alternatively, the wall protrusion element 20' can also be directly attached to or arranged on the container wall 4, which corresponds to a direct connection or attachment. In this case, it is accordingly an integral or one-piece port.

The type of element connection EV between the wall protrusion element 20' and the container wall 4 is described in more detail in FIG. 7b below.

FIG. 5 is a schematic cross-section of a container 1 that is substantially not dimensionally stable, for example a bioreactor and/or a bag without a stirrer with a port or a wall protrusion element 20'. This embodiment relates in particular to a disposable container or a disposable bag. The bioreactor does not comprise a stirring device or a stirring element 3 with the corresponding components. A longitudinal axis $LA_2$ of the container 1 substantially runs between the container top 1" and the container bottom 1'. In particular, the container 1 can be a so-called rocking motion bag, which can be arranged or placed or fastened on an agitator or a shaker bench or a laboratory shaker or a fluctuating and/or vibrating base.

Other features with respect to the wall protrusion element 20' and the sensor attaching device 30 correspond to the corresponding features of the embodiment shown in FIG. 4.

FIG. 6 is a schematic cross-section of a bioreactor container 1, which is substantially not dimensionally stable. It is a bag with a stirrer and an attached or arranged fiber holder or sensor attaching device 30, wherein the fibers or light conductors 24 are aligned with respect to the wall protrusion 20 by means of the sensor attaching device 30 in such a manner that variables of the sample volume V can be recorded by the sensor device 21. This embodiment relates in particular to a disposable container or a disposable bag. The bioreactor also comprises a stirring device or stirring element 3 with components that have already been described in more detail for other embodiments. A stirring shaft 9 extends from the container top 1" to the container bottom 1' substantially along the longitudinal axis $LA_2$ of the container 1.

Other features regarding the wall protrusion element 20' and the sensor attaching device 30 correspond to the corresponding features of the embodiments shown in FIG. 4 and FIG. 5.

FIG. 7a is a schematic side view (from the outside) of an embodiment of a wall protrusion element 20' on a container wall 4 of a container 1, which is only shown here in sections. FIG. 7b corresponds to a section of the object shown in FIG. 7a. Furthermore, FIG. 7b shows a detailed view of a section 20b for attaching the wall protrusion element 20' to the container 1 or the container wall 4 and a connection or element connection EV between the wall protrusion element 20' and the container wall 4.

FIGS. 7a and 7b are schematic representations of an embodiment of a wall protrusion element 20', which is attached to a container wall 4 of a container 1. More precisely, the wall protrusion element 20' is attached to the container 1 by means of an element connection EV shown in the detailed view in FIG. 7b. This element connection EV can be designed to connect the wall protrusion element 20' to the container 1 permanently or over a longer period of time. For example, the element connection EV can comprise a part or a section located on the wall protrusion element 20' and a part or a section located on the container wall 4.

As shown in the detailed view of the area x, the connection EV can be designed in such a manner that the container wall 4 has a toothed or jagged structure or contour over the wall thickness or the thickness of the container wall 4 at one section, wherein the toothed or jagged structure or contour engages in particular with a corresponding complementary toothed or jagged structure or contour over the wall thickness of the wall protrusion element 20' with a perfect fit. In this case, at least the meeting or contacting surfaces or surfaces of the interlocking structures of the wall protrusion element 20' and the container wall 4 can be bonded and/or welded and/or sealed. For example, an adhesive and/or a resin and/or a two-component polymer mixture or other means can be used for permanent or at least temporary adhesive bonding.

Alternatively, the connection EV can be designed so that the wall protrusion element 20' can be easily mounted on and removed from the container wall 4. In this case, a Teflon or silicone grease and/or another inert or sluggishly reacting lubricant can be used for sealing. Additionally or alternatively, a Teflon tape or a Teflon film can be clamped or positioned or placed between the adjacent surfaces of the complementary interlocking structures of both elements to seal the interior 22 of the container 1.

However, as mentioned above, the connection or mounting type of the element connection EV can also comprise a clamp connection and/or a press connection and/or a pressure connection and/or a clip connection and/or a screw connection, wherein a connecting piece is positioned on the section 20b for attaching the wall protrusion element 20' to the container 1 or to the container wall 4, and a complementary connecting counterpart is positioned on the container wall 4. It can also be possible, for example, that the entire wall protrusion element 20' can be screwed into a threaded counterpart of the container wall 4 by means of a thread along the circumference of the wall protrusion element 20'.

The wall protrusion element 20' comprises a substantially spherical wall bulge 20a. In particular, the wall bulge 20a substantially has the shape of a hemisphere, which is characterized by a depth $D_2$, a height $D_3$ and a width $D_4$ (not shown here). The depth $D_2$ corresponds in particular to the radius of the sphere, and the height $D_3$ and the width $D_4$ correspond in particular to the diameter of the sphere. Accordingly, the volume delimited or defined or surrounded by the wall bulge 20a and the two imaginary contour lines or contour surfaces has, in particular and substantially, the volume of a half sphere with the radius corresponding to the depth $D_2$. The wall bulge 20a can alternatively also comprise other shapes, such as a section of an ellipsoid or a spherical section that does not correspond to a hemisphere.

The wall protrusion element 20' furthermore comprises a wall protrusion 20, which extends outward along the longitudinal axis $LA_1$ of the wall protrusion 20. In this case, in contrast to the other embodiments, the longitudinal axis $LA_1$ is inclined in an upward direction toward the container wall 4. This means that the angle α enclosed by the longitudinal axis $LA_1$ or its linear extension and the longitudinal axis $LA_2$ of the container 1 is substantially less than 90°. For example, the angle α can be in a range between approximately 20° and approximately 80°, in particular between approximately 30° and approximately 70°, and preferably between approximately 40° and approximately 60°. The case in which the angle α takes a value of approximately 45° would be particularly preferred. In this case, the angle α lies in the plane represented by the y axis and z axis in the coordinate system indicated. Alternatively, it is also possible for the longitudinal axis $LA_1$ to be inclined in a downward direction toward the container wall 4. In this case, the angle α would be in a range between approximately 160° and approximately 100°, in particular between approximately 150° and approximately 110° and preferably between approximately 140° and approximately 120°. The case in which the angle α takes on a value of approximately 135° would be particularly preferred.

In the embodiment in accordance with FIGS. 7*a* and 7*b*, the longitudinal axis $LA_2$ runs substantially in parallel to the container wall 4 and the imaginary contour line $IK_2$ (as an extension of the container wall 4 along the z axis) along the direction corresponding to the z axis in the coordinate system indicated.

The imaginary contour line $IK_2$ (as an extension of the container wall 4 along the z axis) has a normal $N_2$, which is an axis that is aligned perpendicularly to the imaginary contour line $IK_2$ within the y-z planes (corresponding to the indicated coordinate system). If the angle α enclosed by the longitudinal axis $LA_1$ or its linear extension and the longitudinal axis $LA_2$ of the container 1 amounts to 90°, the normal $N_2$ of the imaginary contour line $IK_2$ is on or at least parallel to a normal $N_1$ of the imaginary contour line $IK_1$ for defining the sample volume V. In the embodiment shown, the normal $N_1$ of the imaginary contour line $IK_1$ for defining the sample volume V corresponds to the longitudinal axis $LA_1$ of the wall protrusion 20. If the angle α deviates from 90°, the two normals $N_1$ and $N_2$ enclose the angle β corresponding to a value of (90°- α).

The wall protrusion 20 can extend in a direction perpendicular to the y-z plane, at least in sections along the circumference of the wall bulge 20*a*. In particular, the wall protrusion can extend in a direction perpendicular to the y-z plane completely along the circumference or "across" the circumference of the wall bulge 20*a*. In particular, the length L of the wall protrusion 20, which extends over the longitudinal axis $LA_1$, can be constant. Alternatively, the length L of the wall protrusion 20 can also vary at different positions along the circumference of the wall bulge 20*a*.

A sensor attaching device 30 is arranged or mounted or attached to the wall protrusion 20 in such a manner that a beam path axis SA of an incident light runs perpendicularly to the window surface of a window 23', in particular of two windows 23'. Accordingly, the sensor attaching device 30 is mounted in an inclined manner on the wall protrusion 20.

In this embodiment, the sensor attaching device 30 does not comprise an attaching device bar 32 but a guide channel or a narrow channel or groove, through which a receiving element 30' of the wall protrusion 20, in particular an elongated bar or protrusion, can be guided. In this manner, the sensor attaching device 30 can be secured or mounted or fixed substantially on the wall protrusion 20, in particular with a small bearing clearance. The position of the sensor attaching device 30 in relation to the elements of the wall protrusion 20 is in this case reversible after each removal and attachment. In particular, the beam path and the beam path axis, for example with regard to window 23', can be reversibly occupied. For example, a position can be reversibly occupied if a magnetic alignment system is provided. Furthermore, a precision bearing can also ensure precise alignment.

The wall protrusion element 20', also referred to as a port, can be in one piece or in multiple parts. If the wall protrusion element 20' is in one piece, as indicated in FIG. 7*b*, in particular in the detailed section x, the wall protrusion element 20' is arranged directly on the container wall 4 of the container 1. If the wall protrusion element 20' is in two parts (not shown), the wall protrusion element 20' is arranged indirectly on the container wall 4 of the container 1, namely by means of a wall section 4' for connection between the wall protrusion element 20' and the container wall 4. The wall section 4' for the connection can preferably be considered as a component of the wall protrusion element 20', which is why the wall protrusion element 20' is then considered to consist of two parts. On the other hand, the wall section 4' for the connection can alternatively also be considered as a component of the container wall 4.

In addition to the longitudinal axis $LA_2$ of the container 1, the contour of the container wall 4, which is directly adjacent to the wall protrusion element 20', can also serve as a reference line for the inclination of the longitudinal axis $LA_1$ of the wall protrusion 20. In this case, the contour of the container wall 4 replaces the longitudinal axis $LA_2$ of the container 1 in such a manner that the angle α between the contour line of the container wall 4 and the longitudinal axis $LA_1$ of the wall protrusion 20 is enclosed.

FIG. 8 is a schematic frontal view of a bioreactor and its container 1 with a wall protrusion 20 inclined with respect to a width axis $A_2$ of the container 1 and the wall bulge 20*a* according to one embodiment.

The container 1 according to one embodiment is now shown in FIG. 8 in a frontal view so that the section is accordingly in the x-z plane of the indicated coordinate system. The container 1 has a width $B_2$ and a length $L_2$.

The bioreactor comprises container 1 and a stirring element. A direction of a possible flow of a medium 8 is indicated by means of an arrow in the diagram.

Furthermore, the container 1 has a longitudinal axis $LA_2$ and a width axis $A_2$ along which a width $B_2$ of the container can be measured. The container 1 also comprises a wall protrusion element 20' comprising a wall protrusion 20 and a wall bulge 20*a*, which has the shape of a cut ellipsoid. The wall protrusion 20 substantially has a width $B_1$ and a width axis $BA_1$ along which the wall protrusion 20 extends. In the embodiment, the wall protrusion 20 is inclined in such a manner that the width axis $BA_1$ encloses an angle γ with the width axis $A_2$ of the container 1, which is substantially a value not equal to zero.

The wall protrusion element 20' in this embodiment can be in one or two parts. In FIG. 8, an arrow on the inner side I of the container 1 indicates a possible direction of rotation of the stirrer, by which the medium 8 is set into a rotary motion. Triggered by rotary motion, upward movement of the medium can occur substantially alongside the wall.

A double arrow on the outer side A indicates a flow angle α t which the medium 8 in particular flows through the slot without great losses.

FIG. 9 is a schematic side view of a section of a container 1 with a wall protrusion 20, the protrusion walls 28 of which each comprise an extension 28', which protrude on the inner side of the container 1 into the inner volume or container interior beyond the imaginary contour line $IK_2$ for defining the sample volume V or, in a filled state, protrude into the medium 8. The extension 28' has a length $L_1$, which can vary. For example, the length $L_1$ of the extension 28' can be approximately 1 cm to 20 cm, in particular the length $L_1$ of the extension 28' can be approximately 2 cm to 10 cm and preferably the length $L_1$ of the extension 28' can be approximately 3 cm to 8 cm. For example, the length $L_1$ of the extension 28' can be approximately ½ to approximately ¹⁄₂₀ of the length L of the wall protrusion 20. In particular, the length $L_1$ of the extension 28' can be approximately ⅓ to approximately ¹⁄₁₀ of the length L of the wall protrusion 20. Preferably, the length $L_1$ of the extension 28' can be approximately ¼ to approximately ⅛ of the length L of the wall protrusion 20.

The wall protrusion 20, the protrusion walls 28 of which each comprise an extension 28', is a component of a wall protrusion element 20' or a port. The wall protrusion element 20' comprises a section 20b for attaching the wall protrusion element 20' to the container 1. By means of the extension 28' of the protrusion walls 28, the flow of the medium 8 can be influenced, in particular substantially along the inner side of the container wall 4. In other words, the wall flow can be slowed and/or deflected by the respective extension 28' of the protrusion walls 28. This can also cause turbulent flows at the edges of the extensions 28', for example. In FIG. 9, a possible flow profile of the medium 8 is indicated by three lines with arrows. The lines initially indicate a deflected laminar flow of the medium 8 along the container wall 4. However, as already mentioned, turbulent flows can also occur, in particular near the extensions 28'.

In particular, it can be avoided that too strong a flow of the medium 8 occurs in the sample volume V or in the slit or slit-shaped sample volume. In other words, through the respective extension 28', a volume of the medium 8 per time unit, which flows through the sample volume at least in sections, can be reduced or decreased. In particular, this allows almost a flow standstill to be achieved within the sample volume V. At least a flow of a medium through the sample volume V can be slowed down considerably.

The embodiment of the wall protrusion 20 comprising the extension 28' of the wall protrusion 20 can also be understood to mean that the wall protrusion itself protrudes into the interior beyond the imaginary contour line $IK_2$ for defining the sample volume V.

In the case that the wall protrusion element 20' comprises a wall bulge 20a, it can also be that, in particular, an edge of the wall bulge 20a comprises an extension 28', which protrudes on the inner side of the container 1 into the container interior beyond the imaginary contour line $IK_2$, for defining the sample volume V or, in a filled state, protrudes into the medium 8.

The respective extension 28' of the protrusion walls 28 can have the shape given by the protrusion walls 28. Alternatively, the extension 28' can deviate from a shape dictated by a protrusion wall 28. For example, the respective extensions 28' of the protrusion walls 28 can also be directed toward and/or against each other so that they are bent or inclined in relation to the protrusion walls 28. In this manner, for example, a flow of the medium 8 can be particularly well-influenced, for example, slowed down near the sample volume V. The area in the sample volume V is therefore "calmed" compared to other areas in the container interior 22 of the container 1.

In particular, the features regarding the orientation of the wall protrusion 20 can be combined from, for example, FIGS. 7a, 7b and 8. In general, it is possible to explicitly combine all features of different embodiments to the extent that they are not mutually exclusive.

FIG. 10a is a perspective side view of a wall protrusion element 20' according to a particular embodiment. The side view substantially relates to a view from the inner side I of the container 1 on the slit-like volume S of the wall bulge 20. At the slit S of the wall bulge 20 is arranged a guide plate or a guide section 34 designed to guide a medium, in particular a liquid, into a channel K or a channel-like volume K within the slit S. In other words, the guide section 34 at least partly forms a channel, which is designed to guide a medium substantially through the slit S and in particular the sample volume V.

FIG. 10b is the frontal view of the wall protrusion element 20' according to the embodiment of FIG. 10a from the inner side of a container 1. The guide plate or guide section 34 is arranged on the left side of the slit S. The guide plate or guide section 34 substantially encloses a part of the slit-shaped volume S and extends along the width axis $B_1$ of the slit S from the left side LS to approximately the middle of the slit S. Alternatively, the guide plate or guide section 34 can also extend not quite to the middle along the width axis $B_1$ of the slit S from the right RS and/or from the left LS.

FIG. 10c is the view of a section through the wall protrusion element 20' along the cut line B-B from FIG. 10b, which substantially corresponds to the width axis $B_1$ of the slit S. The guide section 34 extends along the slit S from the left side LS to approximately the middle of the slit S in the direction of the right side RS. Furthermore, a flow of the medium 8 along a direction of rotation 36 and along a flow direction 37 through the channel K and out of the channel K is indicated by arrows. The medium 8 flows, for example driven by a stirring element 3, substantially clockwise through the container 1. A part of the medium 8 is fed into a channel inlet KE through the guide section 34 into the channel K and in the direction of the channel outlet KA. The channel K substantially runs in such a manner that it guides the medium 8 through the sample volume V and in particular through the section between two windows 23' of the wall protrusion 20. In this manner, new medium 8 can always be flushed into the sample volume V. During a measurement, the flow of the medium 8 can be stopped to ensure a stable measurement.

In the embodiment of FIGS. 10a-10c, the channel K ends in the sample volume V or in the slit S approximately at the middle of the width axis $B_1$ of the slit S such that the medium 8, which is guided through channel K, exits channel K again and possibly causes turbulent flows in the slit S, substantially outside channel K.

FIG. 11a is also a perspective side view of a wall protrusion element 20' according to an additional particular embodiment. The side view substantially relates to a view from the inner side I of the container 1 on the slit-like volume S of the wall bulge 20. At the slit S of the wall bulge 20, a channel guide 35 is arranged, which is designed to guide a medium 8, in particular a liquid, into a channel K or a channel-like volume K within the slit S. In contrast to the embodiment of FIGS. 10a-10c, the channel K according to this embodiment extends substantially over the entire width of the wall protrusion 20 or the slit along the width axis $B_1$ of the slit S. In other words, the sample volume V and/or the slit S comprises a channel K, which has an opening substantially on both sides along the width axis $B_1$. The channel K is substantially enclosed between the openings by channel guide 35.

FIG. 11b is the frontal view of the wall protrusion element 20' according to the embodiment of FIG. 11a from the inner side of a container 1. A channel inlet or outlet KE, KA of channel K is arranged on both sides of the wall protrusion element 20'. The channel guide 35 substantially encloses a part of the slit-shaped volume S and extends along the width axis $B_1$ of the slit S from the left side LS to the right side RS of the slit S.

FIG. 11c is the view of a section through the wall protrusion element 20' along the cut line A-A from FIG. 11b, which substantially corresponds to the width axis $B_1$ of the slit S or extends along the width axis $B_1$. The channel guide 35 stretches along the slit S or along the width axis $B_1$ of the slit S from left side LS to right side RS of the slit S. Further on, a flow of the medium 8 along a direction of rotation 36 and along a flow direction 37 through the channel K and out of the channel K is indicated by arrows. The medium 8 also flows in this case, for example driven by a stirring element 3 substantially clockwise through the container 1. A part of the medium 8 is led into the channel inlet KE, which here for example is located on the left side LS, through the channel guide 35 into channel K and in the direction of the channel outlet KA, here on the right side RS. If the direction of rotation 36 is reversed, the channel inlet KE would be on the right side RS and the channel outlet KA would be on the left side LS. The channel K substantially runs in such a manner that it guides the medium 8 through the sample volume V and in particular through the section between two windows 23' of the wall protrusion 20. In this manner, new medium 8 can always be flushed into the sample volume V.

The channel K in general can have a round or angular cross-section, can widen or narrow in one direction.

In the following, general dimensions that can apply to different embodiments and/or can be combined are listed. The information is general, exemplary and not restrictive.

In general, the depth $D_2$ of the wall bulge 20a can, for example, take on values between approximately 5 mm to approximately 30 cm, in particular between approximately 2 cm and approximately 10 cm and preferably between approximately 3 cm and approximately 5 cm. In general, the height $D_3$ of the wall bulge 20a can, for example, take on values between approximately 1 cm to approximately 100 cm, in particular between approximately 2 cm and approximately 20 cm and preferably between approximately 3 cm and approximately 10 cm. In general, the width $D_4$ of the wall bulge 20a can, for example, take on values between approximately 1 cm to approximately 100 cm, in particular between approximately 2 cm and approximately 20 cm and preferably between approximately 3 cm and approximately 10 cm. In general, the sample layer thickness $D_1$ or the internal distance between the two substantially parallel protrusion walls 28 can, for example, be between approximately 20 μm and approximately 10 cm, in particular between approximately 500 μm and approximately 2 cm, preferably between approximately 1 mm and approximately 1 cm thick. In general, the protrusion length L can, for example, be between approximately 5 mm and approximately 20 cm, in particular between approximately 1 cm and approximately 10 cm and preferably between approximately 3 cm and approximately 8 cm. For example, the protrusion length L is at least approximately twice, in particular at least approximately five times and preferably at least approximately eight times as long or large as the sample layer thickness $D_1$.

In particular, the ratio of height to width, $D_3/D_4$, can correspond to a value of approximately 1. In this case, the wall bulge 20a, for example, would be substantially circular in a frontal view. It is also possible that the ratio of height to width, $D_3/D_4$, takes on values between approximately 0.2 and approximately 1, in particular between approximately 0.33 and approximately 0.8 and preferably between approximately 0.5 and approximately 0.75. Furthermore, the inverse ratio of width to height, $D_4/D_3$, can also take on values between approximately 0.2 and approximately 1, in particular between approximately 0.33 and approximately 0.8 and preferably between approximately 0.5 and approximately 0.75. For example, the ratio of depth to height, $D_2/D_3$, can take on a value of approximately 0.5. In this case, the wall bulge 20a, for example, could protrude circularly from the container inner side I to the outer side A. It is also possible that the ratio of depth to height, $D_2/D_3$, takes on values between approximately 0.05 and approximately 0.5, in particular between approximately 0.07 and approximately 0.4 and preferably between approximately 0.1 and approximately 0.3. Furthermore, the ratio of depth to height, $D_2/D_3$, can also, for example, take on a value that is greater than approximately 0.5. In this case, the wall bulge 20a would be particularly exposed and would come close to the shape of a slit. It is possible that the ratio of depth to protrusion length, $D_2/L$, takes on values between approximately 0.1 and approximately 1, in particular between approximately 0.3 and approximately 0.9 and preferably between approximately 0.33 and approximately 0.75. Furthermore, the ratio of depth to protrusion length, $D_2/L$, can also, for example, take on a value that is greater than approximately 1 and in particular lies between approximately 1.2 and approximately 1.5.

The sample volume V, which is at least partly surrounded or enclosed by the wall protrusion 20, can, for example, take on values between approximately 100 μl and approximately 500 ml, in particular between approximately 200 μl and approximately 200 ml and preferably between approximately 300 μl and approximately 100 ml. The total inner volume or the container interior 22 of a container 1 including the sample volume can, for example, take on values between approximately 500 ml and approximately 2000 l, in particular between approximately 1 l and approximately 1000 l and preferably between approximately 2 l and approximately 500 l. For example, the total inner volume or the container interior 22 can be approximately 10 to approximately $25*10^7$ in particular approximately $1*10^6$ to approximately $1.5*10^7$ and preferably approximately $15*10^6$ to approximately $1*10^7$ times the sample volume V.

In particular, it should be noted that a longitudinal axis $LA_2$ of the container 1 can also be replaced by the width axis $A_2$ of the container 1 so that, for example, when defining the angle α, the width axis $A_2$ or a width axis of the container 1 is used instead of the longitudinal axis $LA_2$ of the container 1. This is the case, for example, if the container 1 is a bag resting on a surface and its longitudinal axis $LA_2$ is substantially parallel to the surface on which the bag rests. This would be a similar case if the container 1 from FIG. 8 were rotated by 90°, assuming that the z axis of the indicated coordinate system corresponds to the opposite direction of gravity. Then, the height of bag 1 extends along the width axis $BA_2$. Accordingly, it is also possible that a wall protrusion is arranged on the top 1" of the container 1 or on the bottom 1' of the container 1. In this case, the top 1" of the container 1 and the bottom 1' of the container 1 are defined by their position in relation to gravity. This means that, in the reference system of the earth, a container top 1" is located "at the top" and a container bottom 1' is located "at the bottom" in a container 1.

LIST OF REFERENCE SIGNS

1 Container, in particular a disposable container
1' Container bottom
1" Container top
2 Drive device
3 Stirring element
4 Container wall
4' Wall section for connection between wall protrusion element and container wall
5 Stirring extension
6 Bearing on the drive side
7 Counter bearing
8 Medium, in particular biological medium
9 Stirring shaft
10 Axial three-phase machine
20 Wall protrusion
20' Wall protrusion element
20a Wall bulge 20b Section for attaching the wall protrusion element to the container
21 Sensor or sensor device or optical measuring device
22 Container interior or container inner volume
23 Sensor region
23' Window
23b Reflective element and/or diffusely reflecting surface and/or mirror
24 Light conductor or optical fiber
24a Light conductor incoupling section
24b Light conductor outcoupling section
25 Spectrometer
26 Access point
27 PH electrode or pH sensor
28 Protrusion walls
28' Extension of the protrusion walls of the wall protrusion
29 Line
30 Sensor attaching device
30' Receiving element for a sensor attaching device
32 Attaching device bar
33 Recess
34 Guide plate or guide section
35 Channel guide
36 Direction of rotation of the medium
37 Flow direction of the medium
A Outer side
α Angle between the longitudinal axis of the wall protrusion and the longitudinal axis of the container
β Angle between the longitudinal axis of the wall protrusion and the normal N2 of the
imaginary contour line IK2
$B_1$ Width of the wall protrusion
$B_2$ Width of the container
γ Angle between width axis of the wall protrusion and width axis of the container
$BA_1$ Width axis of the wall protrusion
$BA_2$ Width axis of the container
$D_1$ Sample layer thickness
$D_2$ Depth of the wall bulge
$D_3$ Height of the wall bulge
$D_4$ Width of the wall bulge
EV Connection between the section for attaching the wall protrusion element to the container wall
I Container inner side
$IK_1$ Imaginary contour line for defining the sample volume
$IK_2$ Imaginary contour line as an extension of the container wall and as a boundary to the wall bulge
K Channel
KE Channel inlet
KA Channel outlet
L Length of the wall protrusion
$L_1$ Length of the extension of the protrusion walls of the wall protrusion
$L_2$ Length of the container
$LA_1$ Longitudinal axis of the wall protrusion
$LA_2$ Longitudinal axis of the container
LS Left side
$N_1$ Normal of the imaginary contour line IK1
$N_2$ Normal of the imaginary contour line IK2
O Upper edge of the container
R Reflective beam path arrangement
RS Right side
S Slit or slit-shaped volume
SG Beam path axis
T Transmissive beam path arrangement
V Sample volume
AV Volume of the wall bulge

The invention claimed is:

1. A container comprising:
a container wall;
a container interior; and
at least one wall protrusion element for attaching at least one sensor from an outer side of the container for sensing at least one variable of a medium contained in the container interior,
wherein the wall protrusion element comprises a wall protrusion and a wall bulge, and the wall bulge comprises a shape that is substantially spherical, substantially hemispherical, a section of an ellipsoid, or a spherical section that does not correspond to a hemisphere,
wherein the wall protrusion is arranged on the container wall and at least partly surrounds the container interior and the medium, and
wherein the at least one wall protrusion element comprises at least one sensor region through which a variable of the medium can be determined using a sensor device that does not contact the medium.

2. The container according to claim 1, wherein the at least one wall protrusion has a longitudinal axis, wherein the longitudinal axis encloses an angle with a normal of an imaginary contour line for defining a sample volume of −45° to 45° and/or a width axis of the at least one wall protrusion encloses an angle of −45° to 45° with a width axis of the container.

3. The container according to claim 1, wherein the at least one sensor region comprises an optical element that includes a window.

4. The container according to claim 1, wherein the at least one wall protrusion comprises two protrusion walls, the two protrusion walls being parallel to each other and spaced apart from each other by a sample layer thickness,
wherein the protrusion walls have a protrusion length such that the wall protrusion surrounds a slit-shaped volume, wherein at least one of the protrusion walls comprises the sensor region.

5. The container according to claim 1, wherein the at least one wall protrusion comprises a diffusely scattering surface, and
wherein the sensor device comprises an optical fiber and the variable is determined by transflection or double transmission by means of reflection at the diffusely scattering surface.

6. The container according to claim 4, wherein the two protrusion walls each comprise a window and the windows are arranged so that the variable can be determined by the sensor device through a transmissive beam path arrangement.

7. The container according to claim 1, comprising a sensor attaching device for attaching the sensor device relative to the at least one wall protrusion.

8. The container according to claim 7, wherein the sensor attaching device comprises at least one receiving device configured to receive an additional optical element, wherein the additional optical element comprises at least one lens, mirror, prism, pinhole, or combination thereof.

9. The container according to claim 1, wherein the container is disposable bioreactor container.

10. The container according to claim 1, wherein the wall protrusion element has at least one access point, wherein the at least one access point is configured to receive a pH electrode to determine a pH value of the medium through the at least one access point.

11. The container according to claim 1, wherein the at least one wall protrusion comprises protrusion walls, which at least in sections each have an extension protruding into a container inner side or wherein the wall protrusion comprises protrusion walls protruding into the container inner side.

12. The container according to claim 1, wherein the at least one wall protrusion comprises a channel, wherein the channel is at least partly surrounded by a channel guide and/or a guide section, and wherein the channel is configured to guide a moving medium from a channel inlet to a channel outlet in one flow direction.

13. A wall protrusion element for fastening on a container wall of a container, the wall protrusion element comprising:
a wall protrusion and a wall bulge,
wherein the wall bulge comprises a shape that is substantially spherical, substantially hemispherical, a section of an ellipsoid, or a spherical section that does not correspond to a hemisphere,
wherein the wall protrusion is configured to receive at least one sensor from an outer side of the container for sensing at least one variable of a medium contained in a container interior,
wherein the wall protrusion is configured to at least partly surround the container interior and to extend outwardly from a container wall contour of the container wall; and
wherein the wall protrusion element comprises at least one sensor region configured so that the variable can be sensed through the sensor region by means of the at least one sensor.

14. The wall protrusion element according to claim 13, wherein the wall protrusion element is configured for removable attachment of the wall protrusion element to the container wall.

15. The wall protrusion element according to claim 13, wherein the wall protrusion element is configured to be permanently fixedly to the container wall.

16. The wall protrusion element according to claim 13, wherein the wall protrusion has a longitudinal axis along which it extends, and wherein the longitudinal axis encloses an angle of −45° to 45° with a normal of an imaginary contour line for defining a sample volume.

17. The wall protrusion element according to claim 13, wherein the wall protrusion element is sterilized.

18. The wall protrusion element according to claim 13, wherein a wall protrusion comprises protrusion walls, which at least in sections have an extension that protrudes onto a container inner side or wherein a wall protrusion comprises protrusion walls, which protrude onto the container inner side.

19. The wall protrusion element according to claim 13, wherein the wall protrusion comprises a channel, which is at least partly surrounded by a channel guide and/or a guide section, and the channel is designed to guide a moving medium from a channel inlet to a channel outlet in one flow direction.

20. A method for providing a sensing of at least one variable of a medium contained in a container interior of a container, comprising the steps of:
arranging a wall protrusion element comprising a wall protrusion and a wall bulge on a container wall of the container so that the wall bulge extends outwardly from a container wall contour of the container wall, wherein the wall bulge comprises a shape that is substantially spherical, substantially hemispherical, a section of an ellipsoid, or a spherical section that does not correspond to a hemisphere;
at least partly surrounding the container interior and the medium by the wall protrusion;
providing at least one sensor region on the wall protrusion;
attaching from an outer side of the container at least one sensor relative to at least one wall protrusion; and
sensing the variable of the medium through the sensor region by means of the at least one sensor.

* * * * *